US005656211A

United States Patent [19]
Unger et al.

[11] Patent Number: 5,656,211
[45] Date of Patent: *Aug. 12, 1997

[54] APPARATUS AND METHOD FOR MAKING GAS-FILLED VESICLES OF OPTIMAL SIZE

[75] Inventors: Evan Unger; Thomas McCreery; David Yellowhair; Terrence R. Barrette, all of Tucson, Ariz.

[73] Assignee: ImaRx Pharmaceutical Corp., Tucson, Ariz.

[*] Notice: The term of this patent shall not extend beyond the expiration date of Pat. No. 5,469,854.

[21] Appl. No.: 482,294

[22] Filed: Jun. 7, 1995

Related U.S. Application Data

[63] Continuation-in-part of Ser. No. 307,305, Sep. 19, 1994, and Ser. No. 160,232, Nov. 30, 1993, Pat. No. 5,542,938, which is a continuation-in-part of Ser. No. 76,250, Jun. 11, 1993, which is a continuation-in-part of Ser. No. 717,084, Jun. 18, 1991, Pat. No. 5,228,446, and Ser. No. 716,899, Jun. 18, 1991, abandoned, said Ser. No. 307,305, is a continuation-in-part of Ser. No. 159,687, Nov. 30, 1993, which is a continuation-in-part of Ser. No. 76,239, Jun. 11, 1993, abandoned, which is a continuation-in-part of Ser. No. 717,084, and Ser. No. 716,899, said Ser. No. 717,084, and Ser. No. 716,899, each is a continuation-in-part of Ser. No.569,828, Aug. 20, 1990, Pat. No. 5,088,499, which is a continuation-in-part of Ser. No. 455,707, Dec. 22, 1989, abandoned.

[51] Int. Cl.⁶ .............. B01J 13/02; B01J 13/04; B01J 13/20; B01J 13/22
[52] U.S. Cl. .............. 264/4.1; 264/4.3; 424/489; 424/490; 424/491; 424/501
[58] Field of Search .............. 264/4.1, 4.3, 4.5; 424/489, 490, 491, 501

[56] References Cited

U.S. PATENT DOCUMENTS

| 3,532,500 | 10/1970 | Priest et al. | 96/91 |
|---|---|---|---|
| 3,873,564 | 3/1975 | Schneider et al. | 260/309.6 |
| 4,089,801 | 5/1978 | Schneider | 252/316 |

(List continued on next page.)

FOREIGN PATENT DOCUMENTS

| 0 107 559 | 5/1984 | European Pat. Off. |
|---|---|---|
| 0 077 752 B1 | 3/1986 | European Pat. Off. |
| 0 243 947 | 4/1987 | European Pat. Off. |
| 0 231 091 | 8/1987 | European Pat. Off. |
| 0 272 091 | 6/1988 | European Pat. Off. |
| 0 320 433 A2 | 12/1988 | European Pat. Off. |
| 0 324 938 | 7/1989 | European Pat. Off. |
| 89-250016.6 | 8/1989 | European Pat. Off. |
| 0 338 971 | 10/1989 | European Pat. Off. |
| 0 361 894 | 4/1990 | European Pat. Off. |
| 0 216 730 | 1/1991 | European Pat. Off. |
| 91-250038.6 | 2/1991 | European Pat. Off. |
| 0 467 031 A2 | 5/1991 | European Pat. Off. |
| 0 357 164 B1 | 10/1991 | European Pat. Off. |
| 0 458 745 A1 | 11/1991 | European Pat. Off. |
| 0 314 764 B1 | 9/1992 | European Pat. Off. |
| 0 554 213 A1 | 8/1993 | European Pat. Off. |
| 63-60943 | 3/1988 | Japan. |
| 2193095 | 2/1988 | United Kingdom. |
| WO80/02365 | 11/1980 | WIPO. |
| WO82/01642 | 5/1982 | WIPO. |
| US85/01161 | 3/1985 | WIPO. |
| WO86/00238 | 1/1986 | WIPO. |
| WO86/01103 | 2/1986 | WIPO. |
| WO89/05040 | 6/1989 | WIPO. |
| WO90/04384 | 5/1990 | WIPO. |
| WO90/04943 | 5/1990 | WIPO. |
| WO9100086 | 1/1991 | WIPO. |
| WO91/12823 | 9/1991 | WIPO. |
| WO91/15244 | 10/1991 | WIPO. |
| WO92/10166 | 6/1992 | WIPO. |
| WO92/17212 | 10/1992 | WIPO. |
| WO92/17213 | 10/1992 | WIPO. |
| WO92/17436 | 10/1992 | WIPO. |
| WO92/21382 | 12/1992 | WIPO. |
| WO93/05819 | 1/1993 | WIPO. |
| WO93/06869 | 4/1993 | WIPO. |
| WO93/13809 | 7/1993 | WIPO. |
| WO93/17718 | 9/1993 | WIPO. |
| WO93/20802 | 10/1993 | WIPO. |
| WO94/09829 | 5/1994 | WIPO. |
| WO94/16739 | 8/1994 | WIPO. |
| WO94/21302 | 9/1994 | WIPO. |
| WO95/06518 | 3/1995 | WIPO. |
| WO95/07072 | 3/1995 | WIPO. |
| WO96/04018 | 2/1996 | WIPO. |
| WO96/09793 | 4/1996 | WIPO. |

OTHER PUBLICATIONS

Frézard, et al., "Permeability and stability in buffer and in human serum of fluorinated phospholipid–based liposomes", Biochimica et Biophysica Acta, 1192, pp. 61–70 (1994).

Frézard, et al., "Fluorinated Phospholipid–Based Vesicles as Potential Drug Carriers: Encapsulation/Sustaining of Drugs and Stability in Human Serum", Art, Cells, Blood Subs., and Immob. Biotech., 22(4), pp. 1403–1408 (1994).

Kost et al., Polymers in Medicine II: Biomedical and Pharmaceutical Applications, "Ultrasonic Modulated Drug Delivery Systems", Chiellini et al., ed., (Plenum Press, New York and London), pp. 387–396 (1985).

Moseley et al., Microbubbles: A Novel MR Susceptibility Contrast Agent, abstract, 1991 Napa, California Meeting of the Society for Magnetic Resonance in Medicine.

(List continued on next page.)

Primary Examiner—Nathan M. Nutter
Attorney, Agent, or Firm—Woodcock Washburn Kurtz Mackiewicz & Norris LLP

[57] ABSTRACT

A method and apparatus for making vesicles suitable for use as contrast agents in which a container containing an aqueous suspension phase and a separate gas phase is shaken using reciprocating motion. The reciprocating motion is produced by a shaker arm that moves the container in two, substantially perpendicular directions, with the motion in the first direction being along an arcuate path. The overall path of the motion occurs in a figure-8 eight pattern. The frequency of shaking is at least approximately 2800 RPM, the length of the shaker arm is at least approximately 6 cm, and the angle through which the shaker arm rotates in the first direction is at least approximately 3°. The total length of travel around the figure-8 pattern is at least 0.7 cm.

39 Claims, 20 Drawing Sheets

U.S. PATENT DOCUMENTS

| | | | |
|---|---|---|---|
| 4,162,282 | 7/1979 | Fulwyler et al. | 264/9 |
| 4,192,859 | 3/1980 | Mackaness et al. | 424/5 |
| 4,224,179 | 9/1980 | Schneider | 252/316 |
| 4,229,360 | 10/1980 | Schneider et al. | 260/403 |
| 4,276,885 | 7/1981 | Tickner et al. | 128/660 |
| 4,310,505 | 1/1982 | Baldeschwieler et al. | 424/1 |
| 4,310,506 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,344,929 | 8/1982 | Bonsen et al. | 424/15 |
| 4,426,330 | 1/1984 | Sears | 260/403 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,533,254 | 8/1985 | Cook et al. | 366/176 |
| 4,534,899 | 8/1985 | Sears | 260/403 |
| 4,544,545 | 10/1985 | Ryan et al. | 424/1.1 |
| 4,569,836 | 2/1986 | Gordon. | |
| 4,572,203 | 2/1986 | Feinstein | 128/661 |
| 4,586,512 | 5/1986 | Du-huu et al. | 128/660 |
| 4,603,044 | 7/1986 | Geho et al. | 424/9 |
| 4,615,879 | 10/1986 | Runge et al. | 424/9 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/462 |
| 4,731,239 | 3/1988 | Gordon | 424/9 |
| 4,737,323 | 4/1988 | Martin et al. | 264/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 264/4.3 |
| 4,781,871 | 11/1988 | West, III et al. | 264/4.3 |
| 4,790,891 | 12/1988 | Halliday et al. | 149/2 |
| 4,830,858 | 5/1989 | Payne et al. | 424/450 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 264/4.3 |
| 4,893,624 | 1/1990 | Lele | 128/399 |
| 4,895,719 | 1/1990 | Radhakrishnan | 424/45 |
| 4,898,734 | 2/1990 | Mathiowitz et al. | 424/426 |
| 4,900,540 | 2/1990 | Ryan et al. | 424/9 |
| 4,921,706 | 5/1990 | Roberts et al. | 424/450 |
| 4,927,623 | 5/1990 | Long, Jr. | 424/5 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,987,154 | 1/1991 | Long, Jr. | 514/772 |
| 4,996,041 | 2/1991 | Arai et al. | 424/9 |
| 5,000,960 | 3/1991 | Wallach | 424/450 |
| 5,008,050 | 4/1991 | Cullis et al. | 264/4.3 |
| 5,013,556 | 5/1991 | Woodle et al. | 424/450 |
| 5,045,304 | 9/1991 | Schneider et al. | 424/9 |
| 5,049,388 | 9/1991 | Knight et al. | 424/450 |
| 5,088,499 | 2/1992 | Unger | 128/662.2 |
| 5,114,703 | 5/1992 | Wolf et al. | 424/5 |
| 5,123,414 | 6/1992 | Unger | 128/654 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,982 | 3/1993 | Erbel et al. | 521/56 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,198,225 | 3/1993 | Meybeck et al. | 424/450 |
| 5,205,287 | 4/1993 | Erbel et al. | 128/632 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,271,928 | 12/1993 | Schneider et al. | 424/9 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,316,771 | 5/1994 | Barenholz et al. | 424/450 |
| 5,334,381 | 8/1994 | Unger | 424/9 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,469,854 | 11/1995 | Unger et al. | 128/662.02 |
| 5,470,582 | 11/1995 | Supersaxo et al. | 424/489 |
| 5,487,390 | 1/1996 | Cohen et al. | 128/662.02 |
| 5,496,535 | 3/1996 | Kirkland | 424/9.37 |
| 5,505,932 | 4/1996 | Grinstaff et al. | 424/9.3 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| B1 4,229,360 | 11/1991 | Schneider et al. | 260/403 |

OTHER PUBLICATIONS

Ter–Pogossian, M., "Physical Principles and Instrumentation", *Computed Body Tomography*, Kee et al., eds., Raven Press, New York, Chapter 1, pp. 1–7, 2nd Edition, 1988.

Aronberg, D.J., "Techniques" *Computed Body Tomography*, Kee et al., eds., Raven Press, New York, Chapter 2, pp. 9–36, 2nd Edition, 1988.

Dittrich, "Cardiac Muscle Ischemia and Infarction", *The Second Annual Int. Symposium on Contrast Agents and Diagnostic Ultrasound*, Atlantic City, NJ (May 7, 1996) (Abstract).

Pantely, "Intravenous Contrast Echocardiography–Tissue Imaging & Quantification of Coronary Blood Flow", *The Second Annual Int. Symposium on Contrast Agents in Diagnostic Ultrasound*, Atlantic City, NJ (May 7, 1996) (Abstract).

Shiina et al., "Hyperthermiaby Low–frequency Synthesized Ultrasound", *IEEE Engineering*, pp. 879–880, vol. 2 (abstract) (1988).

Miller, D.L., "Ultrasonic Detection of Resonant Cavitation Bubbles in a Flow Tube by Their Second–Harmonic Emissions", *Ultrasonics*, Sep. 1981, 217–224.

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, 37 Aminomalonic Acid: Spontaneous Decarboxylation and Reaction with 5-Deoxypyridoxal", *Biochemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High-Pressure Continuous-Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast-Carrying Liposomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long-chain Saturated Phosphatidylcholines by Extrusion Technique", Biochimica et Biophysica Acta, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor-Imaging and Hepatosplenography: Preliminary Clinical Results", *Radiology*, vol. 163, pp. 339–343 (1987).

Mattrey et al., "Perfluoroctylbromide: A Liver/Spleen-Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two-Dimensional Contrast Echocardiography, I: In Vitro Development and Quantitative Analysis of Echo Contrast Agents", *JACC*, vol. 3, No. 1, pp. 14–20 (1984).

Ten Cate et al., "Two-Dimensional Contrast Echocardiography, II: Transpulmonary Studies", *JACC*, vol. 3, No. 1, pp. 21–27 (1984).

Unger et al., "Hepatic Metastases: Liposomal Gd-DTPA-enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd-DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.*, vol. 92, No. 8, pp. 2450–2460 (1970).

Muhlradt et al., "Vitamin B6 Analogs: An Improved Synthesis of 5-Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience*, Sonicator™, Heat Systems-Ultrasonics, Inc. (1987).

M. Ostro, "Liposomes", Marcel Dekker, New York, pp. 102–103 (1983).

Fukuda et al., "Polymer-Encased Vesicles Derived from Diotadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).

J. Vion-Dury et al., *J. Pharmacol. Exper. Ther.*, vol. 250(3), pp. 1113–1118 (1989) (abstract).

M.R. Zalutsky et al., *Invest. Radiol.*, vol. 22(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 1–18, 29–35, 51–65 and 79–107 (CRC Press Inc., Boca Raton, FL, 1984).

Madden et al., *Chemistry and Physics of Lipids*, vol. 53, pp. 37–46 (1990).

Sinkula et al., *J. Pharm. Sci.*, vol. 64, pp. 181–210 (1975).

McAvoy et al., *IEEE Engineering, Ultrasonics Symposium Proceedings*, vol. 2, pp. 677–1248 (abstract).

Chapman et al., "Biomembrane Phase Transitions", *J. Biol. Chem.*, 1974, 249:2512–2521.

Hug et al., "Liposomes for the Transformation of Eukaryotic Cells", *Biochimica et Biophysica Acta*, 1991, 1097:1–17.

Marsh, *CRC Handbook of Lipid Bilayers* CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700-0003-1C, p. 4.

Bangham et al., "Diffusion of Univalent Ions across the Lamellae of Swollen Phospholipids", *J. Mol. Biol.*, 1965, 13:238–252.

Carson et al., *Ultrasound in Med. & Biol.* 3, 1978, 341–350.

deGier et al., "Relations Between Liposomes and Biomembranes", *Annals of The New York Academy of Sciences*, 1978, 308:85–99.

Felgner et al., "Lipofection: A highly efficient, lipid–mediated DNA–transfection procedure", *Proc. Natl. Acad. Sci.*, 1987, 84:7413–7417.

Gabizon et al., "Liposome formulations with prolonged circulation time in blood and enhanced uptake by tumors", *Proc. Natl. Acad. Sci.*, 1988, 85:6949–6953.

Garelli, et al., *Biochimica et Biophysica Acta*, vol. 1127:41–48 (1992).

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination . . . ", *J. Am. Chem. Soc.*, 1991, 113:9027–9045.

*Mammalian Cell Biotechnology: A Practical Approach*, M. Butler, 1991 (Oxford University Press, New York), pp. 57–70.

Mathiowitz et al., "Photochemical Rupture of Microcapsules: A Model System", *Journal of Applied Polymer Science*, 1981, 26:809–822.

May et al., "Cationic Liposomes Enable Bovine Herpesvirus Type 2 DNA to Infect Cells", *Acta virol.*, 1991, 35:107.

Poznansky et al., "Biologica Approaches to the Controlled Delivery of Drugs: A Critical Review", *Pharmacol, Rev.*, 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature*, 1992, 359:67–70.

Thompson, Larry, "At Age 2, Gene Therapy Enters a Growth Phase", *Science* 1992, 258:744–746.

Trubetskoy et al. "Cationic liposomes enhance targeted delivery and expression of exogenous DNA . . . ", *Biochimica et Biophysica Acta* 1992, 131:311–313.

Umemura et al., "Studies on Sonodynamic Cancer Therapy", *IEEE*, 1992, O–7803–0785, pp. 354–355 .

Williams, "Human Gene Therapy: Searching for Better Vectors", *ASM News* [American Society for Microbology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science*, vol. 35, pp. 755–774 (1988).

Sankaram et al., "Cholesterol–Induced Fluid–Phase Immiscibility in Membranes", *Proc. Natl. Acad. Sci.*, vol. 88, pp. 8686–8690 (1991).

*Scientific Apparatus Catalog 92/93* (VWR Scientific, 1991), "Syringes", pp. 1511–1513; Filtration, Syringe Filters, pp 766–768; Filtration, Membranes, pp. 750–753; Filtration, Filter Holders, p. 744.

Gramiak et al., *Radiology*, "Detection of Intracardiac Blood Flow by Pulsed Echo–Ranging", pp. 415–418 (1971).

Feigenbaum et al., *Circulation*, "Identification of Ultrasound Echoes from the Left Ventricle by Use of Intracardiac Injections of Indocyanine Green", vol. XL1, pp. 615–621 (1970).

Santaella, et al., *FEBS* 13463, "Extended In Vivo Blood Circulation Time of Fluorinated Liposomes", vol. 336, No. 3, pp. 481–484 (1993).

Brown and Langer, *Annual Review Medicine*, 1988, 39:221 29, Annual Review, Inc., "Transdermal Delivery of Drugs", pp. 221–229.

APPARATUS AND METHOD FOR MAKING GAS-FILLED VESICLES OF OPTIMAL SIZE

RELATED APPLICATIONS

This application is a continuation-in-part of copending application U.S. Ser. No. 08/307,305, filed Sep. 19, 1994, which in turn is a continuation-in-part of application U.S. Ser. No. 08/159,687, filed Nov. 30, 1993, now U.S. Pat. No. 5,585,112, which is in turn a continuation-in-part of application U.S. Ser. No. 08/076,239, filed Jun. 11, 1993, now U.S. Pat. No. 5,469,854, which in turn is a continuation-in-part of application U.S. Ser. No. 07/717,084 filed Jun. 18, 1991, now U.S. Pat. No. 5,228,446 and application U.S. Ser. No. 07/716,899 filed Jun. 18, 1991, now abandoned, both of which are in turn continuations-in-part of application U.S. Ser. No. 07/569,828 filed Aug. 20, 1990, now U.S. Pat. No. 5,088,499, which in turn is a continuation-in-part of application U.S. Ser. No. 07/455,707 filed Dec. 22, 1989, now abandoned.

This application is also a continuation-in-part of application U.S. Ser. No. 08/160,232 filed Nov. 30, 1993, now U.S. Pat. No. 5,542,935, which in turn is a continuation-in-part of application U.S. Ser. No. 08/076,250 filed Jun. 11, 1993, now U.S. Pat. No. 5,580,575, which in turn is a continuation-in-part of application U.S. Ser. No. 07/717,084 filed Jun. 18, 1991, now U.S. Pat. No. 5,228,446 and application U.S. Ser. No. 07/716,899 filed Jun. 18, 1991, now abandoned, both of which are in turn continuations-in-part of application U.S. Ser. No. 07/569,828 filed Aug. 20, 1990, now U.S. Pat. No. 5,088,499, which in turn is a continuation-in-part of application U.S. Ser. No. 07/455,707 filed Dec. 22, 1989, now abandoned.

The disclosures of each of these applications are hereby incorporated herein by reference in their entirety.

1. Field of the Invention

The current invention is directed to a method and apparatus for making gas-filled vesicles, especially gas-filled vesicles of the type useful for ultrasonic imaging. More specifically, the current invention is directed to a method and apparatus for making gas-filled vesicles by shaking in which the shaking parameters are controlled to provide vesicles of optimum size in a minimum amount of time.

2. Background of the Invention

Ultrasound is a diagnostic imaging technique which provides a number of advantages over other diagnostic methodology. Unlike techniques such as nuclear medicine and x-rays, ultrasound does not expose the patient to potentially harmful exposures of ionizing electron radiation that can potentially damage biological materials, such as DNA, RNA, and proteins. In addition, ultrasound technology is a relatively inexpensive modality when compared to such techniques as computed tomography (CT) or magnetic resonance imaging.

The principle of ultrasound is based upon the fact that sound waves will be differentially reflected off of tissues depending upon the makeup and density of the tissue or vasculature being observed. Depending upon the tissue composition, ultrasound waves will either dissipate by absorption, penetrate through the tissue, or reflect back. Reflection, referred to as back scatter or reflectivity, is the basis for developing an ultrasound image. A transducer, which is typically capable of detecting sound waves in the range of 1 MHz to 10 MHz in clinical settings, is used to sensitively detect the returning sound waves. These waves are then integrated into an image that can be quantitated. The quantitated waves are then converted to an image of the tissue being observed.

Despite technical improvements to the ultrasound modality, the images obtained are still subject to further refinement, particularly in regards to imaging of the vasculature and tissues that are perfused with a vascular blood supply. Hence, there is a need for the formulation of agents that will aid in the visualization of the vasculature and vascular-related organs.

Vesicles are desirable as contrast agents for ultrasound because the reflection of sound at a liquid-gas interface, such as the surface of a vesicle, is extremely efficient.

To be effective as ultrasound contrast agents, the vesicles should be as large and elastic as possible since both these properties (bubble size and elasticity) are important in maximizing the reflectivity of sound from the vesicles. Additionally, the vesicles should be stable to pressure, i.e. retain more than 50% of the gas content after exposure to pressure. It is also highly desirable that the vesicles should re-expand after the release of pressure. Further, it is highly desirable to have a high vesicle concentration in order to maximize reflectivity and, hence, contrast. Therefore, vesicle concentration is an important factor in determining the efficacy of the vesicles. In particular, it is desirable to have more than $100 \times 10^6$ vesicles per mL and, more preferably, more than $500 \times 10^6$ vesicles per mL.

Size, however, remains a crucial factor in determining the suitability of vesicles for imagining. In the regime of vesicles that can pass safely through the capillary vasculature, the reflected signal (Rayleigh Scatterer) can be a function of the diameter of the vesicles raised to the sixth power so that a 4 μm diameter vesicle may possess 64 times the scattering capability of a 2 μm diameter vesicle.

Size is also important because vesicles larger than 10 μm can be dangerous. Large vesicles have a tendency to occlude micro-vessels following intravenous or intravascular injection. Hence, it is important that the vesicles be as large as possible to efficiently reflect sound but small enough to pass through the capillaries.

In this regard, it is highly desirable that 99% of the vesicles be smaller than 10 μm. Further, the mean vesicle size should be at least 0.5 μm, preferably over 1 μm, and more preferably close to 2 μm for most effective contrast. In addition, the volume weighted mean should be on the order of 7 μm.

The elasticity of the vesicles may affect their maximum permissible size since the greater the elasticity of the vesicle, the greater its ability to "squeeze" through capillaries. Unfortunately, a number of factors may prevent the formation of highly elastic vesicles, thereby further reenforcing the importance of optimizing vesicle size.

While uncoated vesicles have maximal elasticity, they are generally unstable. Consequently, efforts are often undertaken to improve the stability of the vesicles, such as by coating, that have the effect of reducing their elasticity. In addition, the use of gas or gas-precursors encapsulated in a proteinaceous shell, with the protein being cross-linked with biodegradable cross-linking agents, has been suggested, as well as the use of non-proteinaceous vesicles cross-linked covalently with biocompatible compounds. It may be assumed that such cross-linkers will add a component of rigidity to the vesicles, thus reducing their elasticity.

While it is known that liposomes can be made by shaking a solution of surfactant in a liquid medium (see, U.S. Pat. No. 4,684,479 (D'Arrigo)), a method for making vesicles having optimal size in a minimal amount of time has not heretofore been developed. Consequently, for all of the foregoing reasons, there is a need for a method and apparatus for making vesicles in which the shaking parameters are controlled so as to produce vesicles of optimum size in a minimum amount of time.

SUMMARY OF THE INVENTION

It is an object of the current invention to provide a method and apparatus for making vesicles in which the shaking variables are controlled so as to produce vesicles of optimum size in a minimum amount of time. This and other objects is accomplished in a method in which a container containing an aqueous suspension phase and a gas phase is shaken using reciprocating motion. The reciprocating motion is produced by a shaker arm that moves the container in two, substantially perpendicular directions. The motion in the first direction occurs along an arcuate path having a radius of curvature of at least 6 cm and encompasses an angle of at least 3°. The overall path of the motion occurs in a figure-8 eight pattern. The frequency of shaking is at least 2800 RPM, the amplitude of the shaking is at least 0.3 cm and the total length of travel of the container during each cycle is at least 0.7 cm.

The current invention also encompasses an apparatus for shaking a container containing an aqueous suspension phase and a gas phase using the method described above. Preferably, the apparatus has a shaker arm having a length of at least 6 cm that rotates through an angle of at least 3°.

DESCRIPTION OF THE PREFERRED EMBODIMENT

Figure 1:
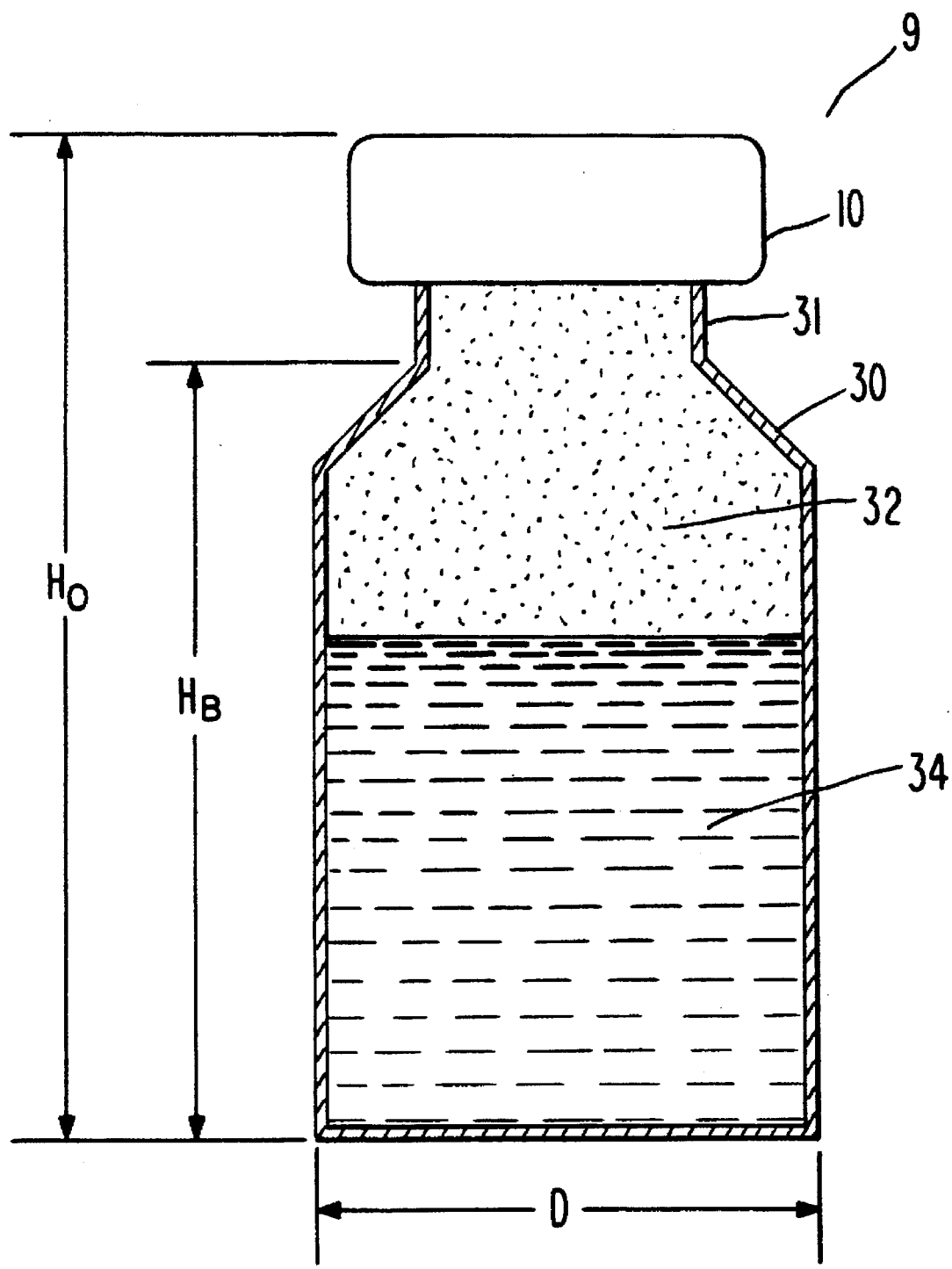
FIG. 1 is a elevation of the container portion of the shaking apparatus of the current invention, in which vesicles are made by the shaking method of the current invention.

According to the method of the current invention, vesicles of optimal size are made by first placing an aqueous suspension 34, preferably comprising lipids, into a container 9, as shown in FIG. 1.

As used herein, the term "vesicle" refers to a spherical entity which is characterized by the presence of an internal void. Preferred vesicles are formulated from lipids, including the various lipids described herein. In any given vesicle, the lipids may be in the form of a monolayer or bilayer, and the mono- or bilayer lipids may be used to form one or more mono- or bilayers. In the case of more than one mono- or bilayer, the mono- or bilayers are generally concentric. The vesicles described herein are also sometimes referred to as bubbles or microbubbles and include such entities commonly referred to as liposomes and micelles, and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a targeting ligand and/or a bioactive agent, as desired.

"Liposome" refers to a generally spherical cluster or aggregate of amphipathic compounds, including lipid compounds, typically in the form of one or more concentric layers. Most preferably the gas filled liposome is constructed of a single layer (i.e. unilamellar) or a single monolayer of lipid. A wide variety of lipids may be used to fabricate the liposomes including phospholipids and non-ionic surfactants (e.g. niosomes). Most preferably the lipids comprising the gas filled liposomes are in the gel state at physiological temperature. The liposomes may be cross-linked or polymerized and may bear polymers such as polyethylene glycol on their surfaces. Targeting ligands directed to endothelial cells are bound to the surface of the gas filled liposomes. A targeting ligand is a substance which is bound to a vesicle and directs the vesicle to a particular cell type such as and not limited to endothelial tissue and/or cells. The targeting ligand may be bound to the vesicle by covalent or non-covalent bonds. The liposomes may also be referred to herein as lipid vesicles. Most preferably the liposomes are substantially devoid of water in their interiors.

"Micelle" refers to colloidal entities which form from lipidic compounds when the concentration of the lipidic compounds, such as lauryl sulfate, is above a critical concentration. Since many of the compounds which form micelles also have surfactant properties (i.e. ability to lower surface tension and both water and fat loving-hydrophilic and lipophilic domains), these same materials may also be used to stabilize bubbles. In general these micellular materials prefer to adopt a monolayer or hexagonal H2 phase configuration, yet may also adopt a bilayer configuration. When a micellular material is used to form a gas filled vesicle, the compounds will generally adopt a radial configuration with the aliphatic (fat loving) moieties oriented toward the vesicle and the hydrophilic domains oriented away from the vesicle surface. For targeting to endothelial cells, the targeting ligands may be attached to the micellular compounds or to amphipathic materials admixed with the micellular compounds. Alternatively, targeting ligands may be adsorbed to the surface of the micellular materials stabilizing the vesicles.

A gas phase is employed above the aqueous suspension phase 34 in the remaining portion, or headspace 32, of the container 9. The introduction of the gas phase can be accomplished by purging the container 9 with a gas, if a gas other than air is to be used for the gas phase, so that the gas occupies the headspace 32 above the aqueous suspension 34. Thus, prior to shaking, the container 9 contains an aqueous suspension phase and a gaseous phase. The container 9 is then installed on the shaker arm 7 of the shaking device 1 of the current invention, a preferred embodiment of which is shown in FIGS. 2, 3 and 6–11, and shaken for a period of time sufficient to form the desired vesicles.

Although filters may be used to further refine the size distribution of the vesicles after shaking, the focus of the current invention is on the control of the shaking parameters in order to produce vesicles of optimal size prior to any post-shaking filtration. Toward this end, the inventors have found that the size of the vesicles produced by shaking is primarily a function of four variables:

(i) the composition of the aqueous suspension phase,
(ii) the composition of the gas phase in the headspace,
(iii) the volume of the container and the relative volume of the headspace that is initially occupied by the gaseous phase, and
(iv) the definition of the primary shaking parameters—i.e., the shape of the path traveled by the container during the shaking, the amplitude of the shaking motion, and the duration and frequency of the shaking.

According to the method of the current invention, each of these variables should be adjusted in a process for making vesicles so as to obtain a desirable vesicle size distribution and concentration, with a preferable vesicle size distribution being one in which the vesicles have a mean size of at least about 0.5 μm and in which at least 95% of the vesicles, and more preferably at least 99% of the vesicles, have a diameter less than 10 μm, and the concentration of vesicles produced is at least $100 \times 10^6$ vesicles per mL and, more preferably, at least $500 \times 10^6$ vesicles per mL. Consequently, in sections I–IV, below, each of these four variables is discussed individually. In section V, a preferred apparatus for practicing the method of the current invention is disclosed. Section VI discusses some applications of the vesicles made according to the current invention.

I. THE COMPOSITION OF THE AQUEOUS SUSPENSION PHASE

A wide variety of bubble coating agents may be employed in the aqueous suspension phase. Preferably, the coating agents are lipids. The lipids may be saturated or unsaturated, and may be in linear or branched form, as desired. Such lipids may comprise, for example, fatty acids molecules that contain a wide range of carbon atoms, preferably between about 12 carbon atoms and about 22 carbon atoms. Hydrocarbon groups consisting of isoprenoid units, prenyl groups, and/or sterol moieties (e.g., cholesterol, cholesterol sulfate, and analogs thereof) may be employed as well. The lipids may also bear polymer chains, such as the amphipathic polymers polyethyleneglycol (PEG) or polyvinylpyrrolidone (PVP) or derivatives thereof (for in vivo targeting), or charged amino acids such as polylysine or polyarginine (for binding of a negatively charged compound), or carbohydrates (for in vivo targeting) such as is described in U.S. Pat. No. 4,310,505, or glycolipids (for in vivo targeting), or antibodies and other peptides and proteins (for in vivo targeting), etc., as desired. Such targeting or binding compounds may be simply added to the aqueous lipid suspension phase or may be specifically chemically attached to the lipids. The lipids may also be anionic or cationic lipids, if desired, so that they may themselves be capable of binding other compounds such as pharmaceuticals, genetic material, or other therapeutics.

Examples of classes of suitable lipids and specific suitable lipids include: phosphatidylcholines, such as dioleoylphosphatidylcholine, dimyristoylphosphatidylcholine, dipalmitoylphosphatidylcholine (DPPC), and distearoylphosphatidylcholine; phosphatidylethanolamines, such as dipalmitoylphosphatidylethanolamine (DPPE), dioleoylphosphatidylethanolamine and N-succinyl-dioleoylphosphatidylethanolamine; phosphatidylserines; phosphatidyl-glycerols; sphingolipids; glycolipids, such as ganglioside GM1; glucolipids; sulfatides; glycosphingolipids; phosphatidic acids, such as dipalmatoylphosphatidic acid (DPPA); palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isopalmitic fatty acids; isostearic fatty acids; cholesterol and cholesterol derivatives, such as cholesterol hemisuccinate, cholesterol sulfate, and cholesteryl-(4'-trimethylammonio)-butanoate; polyoxyethylene fatty acid esters; polyoxyethylene fatty acid alcohols; polyoxyethylene fatty acid alcohol ethers; polyoxyethylated sorbitan fatty acid esters; glycerol polyethylene glycol oxystearate; glycerol polyethylene glycol ricinoleate; ethoxylated soybean sterols; ethoxylated castor oil; polyoxyethylene-polyoxypropylene fatty acid polymers; polyoxyethylene fatty acid stearates; 12-(((7'-diethylaminocoumarin-3-yl)-carbonyl)-methylamino) octadecanoic acid; N-[12-(((7'-diethylamino-coumarin-3-yl) carbonyl)-methyl-amino)octadacanoyl]-2-amino-palmitic acid; 1,2-dioleoyl-sn-glycerol; 1,2-dipalmitoyl-sn-3-succinylglycerol; 1,3-dipalmitoyl-2-succinyl-glycerol; and 1-hexadecyl-2-palmitoyl-glycerophosphoethanolamine and palmitoylhomocysteine; lauryltrimethylammonium bromide (lauryl-=dodecyl-); cetyltrimethylammonium bromide (cetryl-=hexadecyl-); myristyltrimethylammonium bromide (myristyl-=tetradecyl-); alkyldimethylbenzylammonium chlorides, such as wherein alkyl is a $C_{12}$, $C_{14}$ or $C_{16}$ alkyl; benzyldimethyldodecylammonium bromide; benzyldimethyldodecylammonium chloride, benzyldimethylhexadecylammonium bromide; benzyldimethylhexadecylammonium chloride; benzyldimethyltetradecylammonium bromide; benzyldimethyltetradecylammonium chloride; cetyldimethylethylammonium bromide; cetyldimethylethylammonium chloride; cetylpyridinium bromide; cetylpyridinium chloride; N-[1-2,3-dioleoyloxy)-propyl]-N,N,N-trimethylammonium chloride (DOTMA); 1,2-dioleoyloxy-3-(trimethylammonio) propane (DOTAP); and 1,2-dioleoyl-e-(4'-trimethylammonio)-butanoyl-sn-glycerol (DOTB).

As will be apparent to those skilled in the art, once armed with the present disclosures, the foregoing list of lipids is exemplary only, and other useful lipids, fatty acids and derivatives and combinations thereof, may be employed, and such additional compounds are also intended to be within the scope of the term lipid, as used herein. As the skilled artisan will recognize, such lipids and/or combinations thereof may, upon shaking of the container, form liposomes (that is, lipid spheres having an internal void) which entrap gas from the gaseous phase in their internal void. The liposomes may be comprised of a single lipid layer (a lipid monolayer), two lipid layers (a lipid bilayer) or more than two lipid layers (a lipid multilayer).

As a general matter, it is preferred that the lipids remain in the gel state, that is, below the gel state to liquid crystalline state phase transition of temperature ($T_m$) of the lipid material, particularly during shaking. Gel state to liquid crystalline state phase transition temperatures of various lipids are well known. Such temperatures may also be readily calculated using well known techniques. Table 1, below, from Derek Marsh, "CRC Handbook of Lipid Bilayers", page 139, CRC Press, Boca Raton, Fla. (1990), shows, for example, the main chain phase transition temperatures for a variety of representative saturated phosphocholine lipids.

TABLE 1

Saturated Diacyl-sn-Glycero-(3)-Phosphocholines:
Main Chain Melting Transitions

| # Carbons in Acyl Chains | Main Phase Transition Temperature °C. |
| --- | --- |
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

In a preferred embodiment of the invention, the aqueous lipid phase further comprises a polymer, preferably an amphipathic polymer, and preferably one that is directly bound (i.e., chemically attached) to the lipid. Preferably, the amphipathic polymer is polyethylene glycol or a derivative thereof. The most preferred combination is the lipid dipalmitoylphosphatidylethanolamine (DPPE) bound to polyethylene glycol (PEG), especially PEG of an average molecular weight of about 5000 (DPPE-PEG5000). The PEG or other polymer may be bound to the DPPE or other lipid through a covalent linkage, such as through an amide, carbamate or amine linkage. Alternatively, ester, ether, thioester, thioamide or disulfide (thioester) linkages may be used with the PEG or other polymer to bind the polymer to, for example, cholesterol or other phospholipids. A particularly preferred combination of lipids is DPPC, DPPE-PEG5000 and DPPA, especially in a ratio of about 82%:8%:10% (mole %), DPPC:DPPE-PEG5000:DPPA.

Other coating agents that may alternatively, or in addition, be employed in the aqueous suspension phase include polymers such as proteins, natural and seminatural carbohydrates and synthetic polymers. A variety of different proteins might be used in the invention to produce the gas filled vesicles. Such proteins include albumin from natural (human and animal) and recombinant origins, fibrin, collagen, antibodies and elastin. Natural polysaccharides include starch, cellulose, alginic acid, pectin, dextran, heparin and hyaluronic acid. Semi-natural polysaccharides include methylcellulose, hydroxypropylcellulose, carboxmthylycellulose and hydroxyethyl starch. Synthetic polymers include polyvinylpyrrolidone, copolymers of ethylene and propylene glycol (e.g. Pluronic F-68 and the other Pluronics), polyethyleneglycol, polyvinylalcohol, polylactic acid, copolymers of lactic and glycolic acids, polymethacrylate and double ester polymers. Also inorganic media such as hydroxyapatite and calcium pyrophosphate may be used in the invention. In all these cases the bubble coating agents are suspended in the aqueous phase in a container with a head space of the preselected gas and then shaken. This results in formation of the stabilized, coated vesicles. As one skilled in the art would recognize, once armed with the disclosure of this invention a wide variety of different stabilizing agents can be used to make vesicles according to the principles of the invention.

In one experiment with human serum albumin, BRL-Life Technologies, Gaithersburg, Md., a 10 ml glass vial containing an albumin solution and a head space of perfluoropropane gas (vol of liquid=6 ml, 5 mg per ml albumin solution) was shaken for 2 minutes at 2800 RPM with a Wig-L-Bug™ to produce albumin coated perfluoropropane vesicles having a mean diameter of 5 microns, with a concentration of 50 million particles per ml.

In addition, the use of the invention is compatible with a variety of suspending and/or viscosity agents. The phrase suspending agent, as used herein, denotes a compound that assists in providing relative uniformity or homogeneity to the contrast medium. A number of such agents are available, including xanthan gum, acacia, agar, alginic acid, aluminum monostearate, bassorin, karaya, gum arabic, unpurified bentonite, purified bentonite, bentonite magma, carbomer 934P, calcium carboxymethylcellulose, sodium carboxymethylcellulose, carboxymethylcellulose sodium 12, carrageenan, cellulose (microcrystalline), dextran, gelatin, guar gum, hydroxyethylcellulose, hydroxypropylcellulose, hydroxypropylmethylcellulose, magnesium aluminum silicate, methylcellulose, pectin, casein, gelatin, polyethylene oxide, polyvinyl alcohol, povidone, propylene glycol, alginate, silicon dioxide, silicon dioxide colloidal, sodium alginate and other alginates, and tragacanth. As those skilled in the art would recognize, wide ranges of suspending agent can be employed in the contrast medium of the invention, as needed or desired.

The concentrations of these agents will vary depending upon the bubble stabilizing media which are selected and the shaking parameters may also vary depending upon the materials employed. Lipids, because of their biocompatibility, low toxicity, availability as pure and pharmaceutical grade materials are the preferred bubble coating agents to make the gas filled vesicles of this invention.

To prepare the aqueous phase, the lipids, or other coating agent, may be combined with water (preferably distilled water), normal (physiological) saline solution, phosphate buffered saline solution, or other aqueous based solution, as will be apparent to those skilled in the art.

As one skilled in the art would recognize, once armed with the substance of the present disclosure, various additives may be employed in the aqueous suspension phase of the invention to stabilize that phase, or to stabilize the gas-filled vesicles upon shaking. If desired, these additives may be added to the aqueous suspension phase prior to shaking, or may be added to the composition after shaking and resultant preparation of the gas-filled vesicles. The use of such additives will, of course, be dependent upon the particular application intended for the resultant gas-filled vesicles, as will be readily apparent to those skilled in the art.

A number of stabilizing agents which may be employed in the present invention are available, including xanthan gum, acacia, agar, agarose, alginic acid, alginate, sodium alginate, carrageenan, dextran, dextrin, gelatin, guar gum, tragacanth, locust bean, bassorin, karaya, gum arabic, pectin, casein, bentonite, unpurified bentonite, purified bentonite, bentonite magma, colloidal, cellulose, cellulose (microcrystalline), methylcellulose, hydroxyethylcellulose, hydroxypropylcellulose, hydroxypropylmethylcellulose, carboxymethylcellulose, calcium carboxymethylcellulose, sodium carboxymethylcellulose, carboxymethylcellulose sodium 12, as well as other natural or modified natural celluloses, polysorbate, carbomer 934P, magnesium aluminum silicate, aluminum monostearate, polyethylene oxide, polyvinylalcohol, povidone, polyethylene glycol, propylene glycol, polyvinylpyrrolidone, silicon dioxide, silicon dioxide colloidal.

Also, compounds such as such as perfluorooctylbromide (PFOB), perfluorooctyliodide, perfluorotripropylamine, and perfluorotributylamine may be utilized in the lipid phase as stabilizing agents. Perfluorocarbons with greater than five carbon atoms will generally be liquid at body temperature, and such perfluorocarbons are also highly preferred as stabilizing agents. Suitable perfluorocarbons include perfluorohexane, perfluoroheptane, perfluorooctane, perfluorodecalin, and perfluorododecalin. In addition, perfluorinated lipids or partially fluorinated lipids may be used as well to help in stabilization. As will be apparent to those skilled in the art, a wide variety of perfluorinated and partially fluorinated analogs of the lipids described in the present invention may be used. Because of their relative hydrophobic nature with respect to the hydrocarbon lipids, such perfluorinated or partially fluorinated lipids may even provide advantages in terms of stability. Examples of perfluorinated or partially fluorinated lipids are $F_6C_{11}$ phosphatidylcholine(PC) and $F_8C_5PC$. Such analogs are described, for example, in Santaella et al., *Federation of European Biochemical Societies (FEBS)*, Vol. 336, No. 3, pp. 418–484 (1993), the disclosures of which are hereby incorporated herein by reference in their entirety.

A wide variety of biocompatible oils may also be used for the purpose of assisting stabilization, such as peanut oil, canola oil, olive oil, safflower oil, corn oil, almond oil, cottonseed oil, persic oil, sesame oil, soybean oil, mineral oil, mineral oil light, ethyl oleate, myristyl alcohol, isopropyl myristate, isopropyl palmitate, octyldodecanol, propylene glycol, glycerol, squalene, or any other oil commonly known to be ingestible. These may also include lecithin, sphingomyelin, cholesterol, cholesterol sulfate, and triglycerides.

Stabilization may also be effected by the addition of a wide variety of viscosity modifiers (i.e., viscosity modifying agents), which may serve as stabilizing agents in accordance with the present invention. This class of compounds include but are by no means restricted to: 1) carbohydrates and their phosphorylated and sulfonated derivatives; 2) polyethers with molecular weight ranges between 400 and 8000; 3) di- and trihydroxy alkanes and their polymers in the molecular weight range between 800 and 8000. Liposomes may also be used in conjunction with emulsifying and/or solubilizing agents which may consist of, but are by no means limited to, acacia, cholesterol, diethanolamine, glyceryl monostearate, lanolin alcohols, lecithin, mono- and diglycerides, monoethanolamine, oleic acid, oleyl alcohol, poloxamer, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax, Pluronic F61, Pluronic F64 and Pluronic F68.

Other agents which may be added include tonicity agents such as polyalcohols such as glycerol, propylene glycol, polyvinylalcohol, polyethyeneglycol, glucose, mannitol, sorbitol, sodium chloride and the like.

If desired, anti-bactericidal agents and/or preservatives may be included in the formulation. Such agents include sodium benzoate, all quaternary ammonium salts, sodium azide, methyl paraben, propyl paraben, sorbic acid, potassium sorbate, sodium sorbate, ascorbylpalmitate, butylated hydroxyanisole, butylated hydroxytoluene, chlorobutanol, dehydroacetic acid, ethylenediamine tetraacetic acid (EDTA), monothioglycerol, potassium benzoate, potassium metabisulfite, potassium sorbate, sodium bisulfite, sulfur dioxide, and organic mercurial salts.

If desired, an osmolarity agent may be utilized to control the osmolarity. Suitable osmotically active materials include such physiologically compatible compounds as monosaccharide sugars, disaccharide sugars, sugar alcohols, amino acids, and various synthetic compounds. Suitable monosaccharide sugars or sugar alcohols include, for example, erythrose, threose, ribose, arabinose, xylose, lyxose, allose, altrose, glucose, mannose, idose, galactose, talose, trehalose, ribulose, fructose, sorbitol, mannitol, and sedoheptulose, with preferable monosaccharides being fructose, mannose, xylose, arabinose, mannitol and sorbitol. Suitable disaccharide sugars include, for example, lactose, sucrose, maltose, and cellobiose. Suitable amino acids include, for example, glycine, serine, threonine, cysteine, tyrosine, asparagine, glutamine, aspartic acid, glutamic acid, lysine, arginine and histidine. Synthetic compounds include, for example, glycerol, propylene glycol, polypropylene glycol, ethylene glycol, polyethylene glycol and polyvinyl-pyrrolidone. Various other suitable osmotically active materials are well known to those skilled in the art, and are intended to be within the scope of the term osmotically active agent as used herein.

A variety of polymers, such as those discussed above, may also be added for a variety of different purposes and uses.

As those skilled in the art would recognize, a wide range of additive amounts, such as the suspending agents described above, may be employed in the aqueous suspension phase of the invention, as needed or desired, depending upon the particular end use. Such additives generally may comprise from between 0.01% by volume to about 95% by volume of the resultant contrast agent formulation, although higher or lower amounts may be employed. By way of general guidance, a suspending agent is typically present in an amount of at least about 0.5% by volume, more preferably at least about 1% by volume, even more preferably at least about 10% by volume. Generally the suspending agent is typically present in an amount less than about 50% by volume, more preferably less than about 40% by volume, even more preferably less than about 30% by volume. A typical amount of suspending agent might be about 20% by volume, for example. Also, typically, to achieve generally preferred ranges of osmolarity, less than about 25 g/l, more preferably less than about 20 g/l, even more preferably less than about 15 g/l, and still more preferably less than about 10 g/l of the osmotically active materials are employed, and in some instances no osmotically active materials are employed. A most preferred range of osmotically active materials is generally between about 0.002 g/l and about 10 g/l. These, as well as other, suitable ranges of additives will be readily apparent to those skilled in the art, once placed in possession of the present invention.

A wide variety of therapeutic and/or diagnostic agents may also be incorporated into the aqueous suspension phase simply by adding the desired therapeutic or diagnostic agents to that phase. Suitable therapeutic and diagnostic agents, and suitable amounts thereof, will be readily apparent to those skilled in the art, once armed with the present disclosure. These agents may be incorporated into or onto lipid membranes, or encapsulated in the resultant liposomes.

To further improve the magnetic effect of the resultant gas-filled vesicles for MRI, for example, one or more MRI contrast enhancing agents, such as paramagnetic or superparamagnetic contrast enhancing agents, may be added. Useful MRI contrast enhancing agents include paramagnetic ions such as transition metals, including iron ($Fe^{+3}$), copper ($Cu^{+2}$), and manganese ($Mn^{+2}$) and the lanthanides such as gadolinium ($Gd^{+3}$) and dysprosium ($Dy^{+3}$), nitroxides, iron oxides ($Fe_3O_4$), iron sulfides and paramagnetic particles such as manganese ($Mn^{+2}$) substituted hydroxyapatites. As well, agents such as chromium ($Cr^{+3}$), nickel ($Ni^{+2}$), cobalt ($Co^{+2}$) and europium ($Eu^{+2}$) are other examples of paramagnetic ions that may be used. Other contrast enhancing agents such as nitroxide radicals or any other atom that maintains an unpaired electron spin with paramagnetic properties may be used. Ideally, the contrast enhancing agent is added to the aqueous suspension phase prior to shaking, and is designed such that after shaking, the contrast enhancing agent is incorporated into or onto the surface of the resultant gas-filled vesicles, although addition after vesicle preparation is also possible. The resulting gas-filled vesicles may have greatly enhanced relaxivity, providing an especially effective contrast agent for magnetic resonance imaging. By way of example, manganese ($Mn^{+2}$) will incorporate itself onto the head groups of the lipid when phosphatidylcholine or phosphatidylserine is used in the aqueous lipid phase. If desired, the metals may be chelated using liposoluble compounds as shown, for example, in Unger et al., U.S. Pat. No. 5,312,617, the disclosure of which is hereby incorporated herein by reference in its entirety. Such liposoluble compounds are quite useful, as they will readily incorporate into the liposome membrane. Iron oxides and other particles should generally be small, preferably less than about 1 μ, more preferably less than about 200 nm, and most preferably less than 100 nm, to achieve optimal incorporation into or onto the liposome surface. For improved incorporation, iron oxides coated with aliphatic or lypophyllic compounds may be used as these will tend to incorporate themselves into the lipid coating of the bubble surface.

It also is within the realm of the present invention that the aqueous suspension phase may contain an ingredient to cause gelation, such as an ingredient that will cause gelation with lipid polymers and metals which do not spontaneously gel, or that will enhance gelation. Gelling agents such as polyvalent metal cations, sugars and polyalcohols may be employed. Exemplary polyvalent metal cations useful as gelling agents include calcium, zinc, manganese, iron and magnesium. Useful sugars include monosaccharides such as glucose, galactose, fructose, arabinose, allose and altrose, disaccharides such as maltose, sucrose, cellobiose and lactose, and polysaccharides such as starch. Preferably, the sugar is a simple sugar, that is, monosaccharide or a disaccharide. Polyalcohol gelling agents useful in the present invention include, for example, glycidol, inositol, mannitol, sorbitol, pentaerythritol, galacitol and polyvinylalcohol. Most preferably, the gelling agent employed in the present invention is sucrose and/or calcium. The particular gelling agents which may be employed in the various formulations of the present invention will be readily apparent to one skilled in the art, once armed with the present disclosure.

Combinations of lipids, e.g. phosphatidic acid with calcium or magnesium salts and polymers such as alginic acid, hyaluronic acid or carboxymethyl cellulose may be used to stabilize lipids. It is hypothesized that the divalent cations form metal bridges between the lipids and polymers to stabilize the gas-filled liposomes within the lipid/polymeric systems. Similarly, suspensions containing mixtures of chitosan (or chitin-based materials), polylysine, polyethyleneimine and alginic acid (or its derivatives) or hyaluronic acid may be prepared.

It has been discovered that the different materials within the aqueous phase may be important in controlling resultant gas-filled vesicle size. Table 2 shows the sizes of liposomes produced by shaking sterile containers filled with an aqueous phase and a headspace of nitrogen. In all cases, the liposome size was measured by a Particle Sizing System Model 770 light obscuration particle sizer (Particle Sizing Systems, Santa Barbara, Calif.). As the data reveals, the ratio of lipids in the aqueous phase affects the size distribution of the resulting gas-filled liposomes. Specifically, Table 2 below shows the effect of lipid composition on the average liposome size.

TABLE 2

| Effect of Lipid Composition on Average Liposome Size | |
| --- | --- |
| Lipid Composition* | Average Liposome Size |
| 77.5:15:7.5 | 5.26 μm |
| 77.5:20:2.5 | 7.33 μm |
| 82:10:8 | 6.02 μm |

*Ratios of dipalmitoylphosphatidylcholine:dipalmitoyl-phosphatidic acid:dipalmitoylphosphatidylethanolamine-PEG5000, in mole %.

Table 3 demonstrates the dependence of the concentration of a defined lipid composition mixture upon the average liposome size. As shown in Table 3, variations in the total concentrations of lipid are also important in affecting liposome size after shaking. In these experiments the ratio of the three different lipid components was held constant and the concentration of lipid was varied between 0.5 and 5.0 mg ml$^{-1}$ in the aqueous phase. The gas used was nitrogen. The optimal size vesicles for ultrasonic diagnosis with a headspace of perfluorobutane was produced when the lipid concentration in the aqueous phase was 1.0 mg ml$^{-1}$.

TABLE 3

Effect of Lipid Concentration on Average Liposome Size

| Lipid Concentration* | Average Liposome Size |
| --- | --- |
| 1 mg ml$^{-1}$ | 1.8 μm |
| 3 mg ml$^{-1}$ | 4.0 μm |
| 5 mg ml$^{-1}$ | 7.2 μm |

*Lipid concentration for all samples was based upon a mole % ratio of dipalmitoylphosphatidylcholine:dipalmitoylphosphatidic acid: dipalmitoylphosphatidylethanolamine-PEG5000 of 82:10:8. The gas used was nitrogen.

The size of vesicles may also depend on the concentration of stabilizing media, e.g. lipids. For example it has been discovered that a 1.0 mg ml$^{-1}$ lipid concentration produces gas-filled liposomes of about the same diameter when nitrogen is used, as the 5.0 mg ml$^{-1}$ concentration of lipids with perfluorobutane. However, it has been found that the higher concentration may result in a distribution skewed a bit more towards larger gas-filled liposomes. This phenomenon tends to reflect the increased stability of the gas-filled liposomes at higher lipid concentration. It is therefore believed that the higher concentration of lipid either contributes to the stability by acting as a stabilizing agent in the aqueous phase or, the higher lipid concentration provides more lamellae around the gas, making them more stable, and thus allowing a greater proportion of the larger liposomes to persist.

It is also believed that the surface tension at the gas-filled vesicle interface and the aqueous milieu is an additional determining factor in the ultimate size of the gas-filled vesicle, when taken into account along with the other variables.

II. THE COMPOSITION OF THE GASEOUS PHASE

A wide variety of different gases may be employed in the gaseous phase of the present invention. Preferably the gases are substantially insoluble in the aqueous suspension phase. By substantially insoluble, it is meant that the gas maintains a solubility in water at 20° C. and 1 atmosphere of pressure of equal to or less than about 18 ml of gas per kg of water. As such, substantially insoluble gases have a solubility which is less than the solubility of nitrogen gas. Preferably, the solubility is equal to or less than about 15 ml of gas per kg of water, more preferably equal to or less than about 10 ml of gas per kg of water, at 20° C. and 1 atmosphere of pressure. In one preferable class of gases, the solubility is between about 0.001 and about 18 ml of gas per kg of water, or between about 0.01 and about 15 ml of gas per kg of water, or between about 0.1 and about 10 ml of gas per kg of water, or between about 1 and about 8 ml of gas per kg of water, or between about 2 and 6 ml per kg of water, at the aforementioned temperature and pressure. Perfluorocarbon gases and the fluorinated gas sulfur hexafluoride are, for example, less soluble than 10 ml of gas per kg of water, at 20° C. and 1 atmosphere of pressure, and thus are preferred. Gases which are not substantially insoluble, as defined herein, are referred to as soluble gases.

Other suitable substantially insoluble or soluble gases include, but are not limited to, hexafluoroacetone, isopropylacetylene, allene, tetrafluoroallene, boron trifluoride, 1,2-butadiene, 1,3-butadiene, 1,2,3-trichlorobutadiene, 2-fluoro-1,3-butadiene, 2-methyl-1,3 butadiene, hexafluoro-1,3-butadiene, butadiyne, 1-fluorobutane, 2-methylbutane, decafluorobutane (perfluorobutane), decafluorousobutane (perfluoroisobutane), 1-butene, 2-butene, 2-methy-1-butene, 3-methyl-1-butene, perfluoro-1-butene, perfluoro-1-butene, perfluoro-2-butene, 4-phenyl-3-butene-2-one, 2-methyl-1-butene-3-yne, butylnitrate, 1-butyne, 2-butyne, 2-chloro-1,1,1,4,4,4-hexafluoro-butyne, 3-methyl-1-butyne, perfluoro-2-butyne, 2-bromo-butyraldehyde, carbonyl sulfide, crotononitrile, cyclobutane, methylcyclobutane, octafluorocyclobutane (perfluorocyclobutane), perfluoroisobutane, 3-chlorocyclopentene, cyclopropane, 1,2-dimethylcyclopropane, 1,1-dimethylcyclopropane, ethyl cyclopropane, methylcyclopropane, diacetylene, 3-ethyl-3-methyldiaziridine, 1,1,1-trifluorodiazoethane, dimethylamine, hexafluorodimethylamine, dimethylethylamine, bis-(dimethyl phosphine)amine, 2,3-dimethyl-2-norbornane, perfluoro-dimethylamine, dimethyloxonium chloride, 1,3-dioxolane-2-one, 1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1-chloro-1,1,2,2-tetrafluoroethane, 2-chloro-1,1-difluoroethane, chloroethane, chloropentafluoroethane, dichlorotrifluoroethane, fluoroethane, nitropentafluoroethane, nitrosopentafluoroethane, perfluoroethane, perfluoroethylamine, ethyl vinyl ether, 1,1-dichloroethylene, 1,1-dichloro-1,2-difluoroethylene, 1,2-difluoroethylene, methane, methane-sulfonyl-chloride-trifluoro, methane-sulfonyl-fluoride-trifluoro, methane(pentafluorothio)trifluoro, methane-bromo-difluoro-nitroso, methane-bromo-fluoro, methane-bromo-chloro-fluoro, methane-bromo-trifluoro, methane-chloro-difluoro-nitro, methane-chloro-dinitro, methane-chloro-fluoro, methane-chloro-trifluoro, methane-chloro-difluoro, methane-dibromo-difluoro, methane-dichloro-difluoro, methane-dichloro-fluoro, methane-difluoro, methane-difluoro-iodo, methane-disilano, methane-fluoro, methane-iodomethane-iodo-trifluoro, methane-nitro-trifluoro, methane-nitroso-trifluoro, methane-tetrafluoro, methane-trichlorofluoro, methane-trifluoro, methanesulfenylchloride-trifluoro, 2-methyl butane, methyl ether, methyl isopropyl ether, methyl lactate, methyl nitrite, methyl sulfide, methyl vinyl ether, neopentane, nitrogen (N$_2$), nitrous oxide, 1,2,3-nonadecane tricarboxylic acid-2-hydroxytrimethylester, 1-nonene-3-yne, oxygen (O$_2$), oxygen 17 ($^{17}$O$_2$), 1,4-pentadiene, n-pentane, dodecafluoropentane (perfluoropentane), tetradecafluorohexane (perfluorohexane), perfluoroisopentane, perfluoroneopentane, 2-pentanone-4-amino-4-methyl, 1-pentene, 2-pentene {cis}, 2-pentene {trans}, 1-pentene-3-bromo, 1-pentene-perfluoro, phthalic acid-tetrachloro, piperidine-2,3,6-trimethyl, propane, propane-1,1,1,2,2,3-hexafluoro, propane-1,2-epoxy, propane-2,2 difluoro, propane-2-amino, propane-2-chloro, propaneheptafluoro-1-nitro, propane-heptafluoro-1-nitroso, perfluoropropane, propene, propyl-1,1,1,2,3,3-hexafluoro-2,3 dichloro, propylene-1-chloro, propylene-chloro-{trans}, propylene-2-chloro, propylene-3-fluoro, propyleneperfluoro, propyne, propyne-3,3,3-trifluoro, styrene-3-fluoro, sulfur hexafluoride, sulfur (di)-decafluoro(S$_2$F$_{10}$), toluene-2,4-diamino, trifluoroacetonitrile, trifluoromethyl peroxide, trifluoromethyl sulfide, tungsten hexafluoride, vinyl acetylene, vinyl ether, neon, helium, krypton, xenon (especially rubidium enriched hyperpolarized xenon gas), carbon dioxide, helium, and air. Fluorinated gases (that is, a gas containing one or more fluorine molecules, such as sulfur hexafluoride), fluorocarbon gases (that is, a fluorinated gas which is a fluorinated carbon or gas), and perfluorocarbon gases (that is, a fluorocarbon gas which is fully fluorinated, such as perfluoropropane and perfluorbutane) are preferred.

While virtually any gas may be theoretically employed in the gaseous phase of the present invention, a particular gas may be chosen to optimize the desired properties of the resultant contrast medium and to fit the particular diagnostic application. It has been found, for example, that certain gases make more stable gas-filled vesicles upon shaking than other gases, and such gases are preferred. It has also been found that certain gases provide better imaging results on diagnostic imaging such as ultrasound or MRI.

As an example of increasing stability of the gas-filled vesicles, it has been found that carbon dioxide<oxygen<air<nitrogen<neon=helium<perfluorocarbon gases. For these, as well as other, reasons fluorinated gases, particularly perfluorocarbon gases, are preferred.

Also, although in some cases soluble gases will function adequately as the gaseous phase in the present invention, substantially insoluble gases tend to result in greater stability than gases with higher solubility, particularly upon creation of the contrast agent on shaking. Also, it will be easier to keep a gaseous phase with such insoluble gases substantially separate from the aqueous suspension phase prior to shaking, in accordance with the present invention. Thus, substantially insoluble gases, as earlier defined, are preferred.

The quality of ultrasound images and the duration of such images also correlates with the solubility of the gas in the aqueous milieu. The decrease in gas solubility, in general, offers a better resolved image of longer duration on ultrasound.

Additionally, it has been generally observed that the size of a gas-filled vesicles produced by shaking correlates with the solubility of the gas in the aqueous milieu, with the gases of greater solubility resulting in larger gas-filled vesicles.

It is also believed that the size of the vesicles may be influenced by the interaction of the gas with the inner wall of the vesicles. Specifically, it is believed that the interaction at the interface affects the tension and, consequently, the outward force of the interior gas on the interior vesicle wall of the vesicle. A decrease in tension allows for smaller vesicles by decreasing the force exerted by the interior gas, thus allowing the force exerted on the exterior of the vesicle by the aqueous milieu to contract the gas-filled vesicle.

The solubility of gases in aqueous solvents may be estimated by the use of Henry's Law, since it is generally applicable to pressures up to about 1 atmosphere pressure and for gases that are slightly soluble (Daniels, F. and Alberty, R. A., Physical Chemistry, 3rd Edition, Wiley & Sons, Inc., New York, 1966). As an example, oxygen has a solubility of 31.6 ml per kg of water at 25° C., atmospheric air possesses a solubility of 21.36 ml in 1 kg of water at 25° C., nitrogen maintains a solubility of approximately 18.8 ml $kg^{-1}$ at 25° C. Sulfur hexafluoride, on the other hand, has a solubility of approximately 5.4 ml $kg^{-1}$ at 25° C.

In sum, the fluorinated gases, fluorocarbon gases, and perfluorocarbon gases are preferred for reasons of stability, insolubility, and resultant vesicle size. Particularly preferred are the fluorinated gas sulfur hexafluoride, and the perfluorocarbon gases perfluoropropane, perfluorobutane, perfluorocyclobutane, perfluoromethane, perfluoroethane, and perfluoropentane, especially perfluoropropane and perfluorobutane.

It should be noted that perfluorocarbons having less than five carbon atoms are gases at room temperature. Perfluoropentane, for example, is a liquid until about 27° C. Above this temperature it will occupy the headspace of the container. It has been demonstrated that perfluoropentane also may be used to fill the headspace (that is, the space in the vial above the lipid suspension phase) even at room temperature, however. By selecting a defined value of liquid perfluoropentane calculated to fill the headspace and adding the liquid to the container at low temperature, e.g., −20° C., and then evacuating the container (effectively removing the headspace of air) and then sealing the container, perfluoropentane will undergo a transition from liquid phase to vapor phase at a temperature lower than its boiling point at 1 atmosphere. Thus, at room temperature it will occupy some or all of the headspace with gas. As those skilled in the art will recognize, one may estimate the decrease in the liquid phase to vapor phase transition temperature by using a common "rule of thumb" estimate. Specifically, for every decrease in pressure by half, the boiling temperature will decrease by about 10° C. Alternatively, one may calculate the decrease in temperature as a function of decreased pressure by using relationships based upon the ideal gas law based upon Boyle's law. Another method for filling the headspace with perfluoropentane is to first evacuate the headspace and then to fill the headspace with perfluoropentane gas above 27° C. Of course, this method is not limited to perfluoropentane alone, but applies to all perfluorocarbon gases, as well as gases in general, provided the boiling point of the gas is known.

If desired, two or more different gases may be used together to fill the headspace. A mixture of gases may have a number of advantages in a wide variety of applications of the resultant gas-filled vesicles (such as applications in ultrasound imaging, MR imaging, etc.). It has been found that a small amount of a substantially insoluble gas may be mixed with a soluble gas to provide greater stability than would be expected by the combination. For example, a small amount of perfluorocarbon gas (generally at least about 1 mole %, for example) may be mixed with air, nitrogen, oxygen, carbon dioxide or other more soluble gases. The resulting gas-filled vesicle contrast agent produced post-shaking may then be more stable than the air, nitrogen, oxygen, carbon dioxide or other more soluble gases alone.

Additionally, the use of a mixture of gases may be used to compensate for the increase in gas-filled vesicle size which might otherwise occur in vivo were pure perfluorocarbon gas containing vesicles to be injected in vivo. It has been found that some perfluorocarbon gases may tend to absorb or imbibe other gases such as oxygen. Thus, if the perfluorocarbon gas is injected intravenously, it may take up the oxygen or other soluble gases dissolved in the circulating blood. The resulting vesicles may then grow in vivo as a result of this uptake. Armed with a knowledge of this phenomenon, one may then premix the perfluorocarbon gas with a soluble gas, such as air, nitrogen, oxygen, carbon dioxide, thereby saturating the perfluorocarbon of its absorptive or imbibing properties. Consequently, this would retard or even eliminate the potential for expansion of the gas-filled vesicles in the bloodstream. This is significant in light of the fact that should a vesicle grow to a size greater than 10 μM, potentially dangerous embolic events may occur if administered in the bloodstream. By filling the headspace with more soluble gases than perfluorocarbon gas, along with the perfluorocarbon gas, the gas-filled vesicles will generally not undergo this increase in size after injection in vivo. Thus, as a result of the present invention, the problem of embolic events as a result of vesicle expansion may be circumvented by producing vesicles where such expansion is eliminated or sufficiently retarded.

Thus, in accordance with the present invention, if desired, a substantially insoluble gas may be combined with a soluble gas to efficiently produce highly effective and stable gas-filled vesicles.

Multiple samples of lipid solutions (1 mg per mL; 82:10:8 mole % ratios of DPPC:DPPA:DPPE-PEG-5000) in 8:1:1 weight ratios of normal saline:glycerol:proplyene glycol in 2 ml vials (actual size 3.7 ml) Wheaton Industries (Millville, N.J.) were placed on a modified Edwards Model SO4 lyophilizer with four cubic foot capacity and subjected to reduced pressure. The headspaces of the vials, which formed 60% of the total volume, were then instilled with 80% PFP with 20% air, 60% PFP with 40% air, 50% PFP with 50% air, 20% PFP with 80% air, or 100% air. The percentages of gas in the headspaces of the different samples were confirmed by gas chromatography a Hewlett Packard Gas Chromatograph Model 1050L interfaced with Hewlett Packard Chem™ softward. The mode of detection was Flame ionization detection. The samples were then shaken at 3,300 RPM for 60 seconds using a standard Wig-L-Bug™ model 3110B and the sizes and vesicles counts determined by optical particle sizing. An Optical Particle Sizer (Particle Sizing Systems, Santa Barbara, Calif.) was used to analyze gas-filled vesicle size and total counts. A sample volume of 5 microliters was used for each analysis, with four samples used for each determination. The results are shown above in Table 4.

As shown in Table 4, even when only 20% of the gas was PFP (a substantially insoluble gas) and 80% of the gas was air (a mixture of soluble gases), 100 fold more vesicles were produced than when air alone (0% PFP) was used. Moreover, when air alone (0% PFP) was used, the vesicles were much less stable and a larger fraction were above 10 microns. The 20% PFP and 80% air vesicles, however, appeared just as stable as the 80% PFP and 20% air vesicles, as well as the other intermediate PFP concentration samples, and the 20% PFP with 80% air produced about as many gas-filled vesicles as 80% PFP with 20% air.

In short, it has been found that only a small amount of a relatively insoluble gas (such as PFP) is needed to stabilize the vesicles, with the vast majority of the gas being a soluble gas. Although the effective solubility of the combination of two or more gases, as calculated by the formula below:

$$\frac{(\text{solubility gas } A) \times (\text{mole percent gas } A) + (\text{solubility gas } B) \times (\text{mole percent gas } B)}{100}$$

may be only slightly different than the solubility of the soluble gas, there is still a high gas-filled vesicle count and gas-filled vesicle stability with only a small amount of insoluble gas in added.

Although not intending to be bound by any theory of operation, it is believed that the substantially insoluble gas is important for a membrane stabilizing effect. Indeed, it is believed that the substantially insoluble gas (such as PFP) acts as a barrier against the lipid membrane, possibly effectively forming a layer on the inner surface of the membrane, which retards egress of the soluble gas (such as air, nitrogen, etc.). This discovery is both surprising and useful, as this allows one to use only a small amount of the substantially insoluble gas (e.g., a perfluorocarbon or other fluorinated gas) and primarily a more biocompatible (less potentially toxic) gas such as air or nitrogen to comprise most of the vesicle volume.

The amount of substantially insoluble gases and soluble gases in any mixture may vary widely, as one skilled in the art will recognize. Typically, however, at least about 0.01% of the total amount of the gas is a substantially insoluble gas, more preferably at least about 0.1%, even more preferably at least about 1%, and most preferably at least about 10%. Suitable ranges of substantially insoluble gas vary, depending upon various factors such as the soluble gas to be

TABLE 4

Effect of Percent Perfluoropropane on Vesicle Size and Number

| Gas % PFP | Number Weighted Mean | Volume Weighted Mean | Estimated Number of Particles | Percentage of Particles <10 μm | Estimated # of Particles per mL | Percentage of Particles >10 μm |
|---|---|---|---|---|---|---|
| 80% | | | | | | |
| Average | 2.37 | 28.76 | 5.45E+0.5 | 98.94 | 1.10E+09 | 1.05 |
| STDev | 0.07 | 0.82 | 4.67E+04 | 0.08 | 8.20E+07 | 0.07 |
| CV | 3% | 3% | 9% | 0% | 7% | 7% |
| 60% | | | | | | |
| Average | 2.14 | 20.75 | 5.87E+05 | 99.36 | 1.15E+09 | 0.64 |
| STDev | 0.02 | 5.93 | 7.08E+04 | 0.10 | 1.27E+08 | 0.09 |
| CV | 1% | 29% | 12% | 0% | 11% | 14% |
| 50% | | | | | | |
| Average | 2.13 | 30.35 | 5.23E+05 | 99.29 | 1.07E+09 | 0.68 |
| STDev | 0.07 | 12.15 | 1.49E+04 | 0.11 | 4.37E+07 | 0.10 |
| CV | 3% | 40% | 3% | 0% | 4% | 15% |
| 20% | | | | | | |
| Average | 2.00 | 13.64 | 5.35E+05 | 99.61 | 1.07E+09 | 0.41 |
| STDev | 0.04 | 6.79 | 2.26E+04 | 0.06 | 3.92E+07 | 0.07 |
| CV | 2% | 50% | 4% | 0% | 4% | 16% |
| 0% | | | | | | |
| Average | 2.30 | 93.28 | 5.03E+03 | 98.23 | 1.00E+07 | 1.93 |
| STDev | 0.21 | 66.05 | 4.96E+02 | 0.26 | 8.60E+05 | 0.36 |
| CV | 9% | 71% | 10% | 0% | 9% | 19% |

In Table 4, STDev = Standard Deviation, and CV = Coefficient of Variance. Also in Table 4, E+ denotes an exponent to a certain power, for example, 5.45E+05 = 5.45 × $10^5$.

additionally employed, the type of lipid, the particular application, etc. Exemplary ranges include between about 0.01% to about 99% substantially insoluble gas, preferably between about 1% and about 95%, more preferably between about 10% and about 90%, and most preferably between about 30% and about 85%.

For other uses beyond diagnostic ultrasound imaging, such as uses in diagnostic magnetic resonance imaging (MRI), paramagnetic gases such as the strongly paramagnetic oxygen 17 gas ($^{17}O_2$), neon, xenon, helium, argon (especially rubidium enriched hyperpolarized xenon gas), or oxygen (which is still, albeit less strongly, paramagnetic), for example, are preferably used to fill the headspace, although other gases may be also used. Most preferably, $^{17}O_2$ gas, neon, rubidium enriched hyperpolarized xenon gas, or oxygen gas is combined with a substantially insoluble gas such as, for example, a perfluorocarbon gas. Paramagnetic gases are well known in the art and suitable paramagnetic gases will be readily apparent to those skilled in the art. The most preferred gas for MRI applications, whether used alone or in combination with another gas, is $^{17}O_2$.

By using a combination of gases, the $^{17}O_2$ or other paramagnetic gas provides the optimal contrast and the perfluorocarbon stabilizes the $^{17}O_2$ gas within the entrapped gas after shaking. Without the addition of the perfluorocarbon gas, gases such as $^{17}O_2$ is generally much less effective, since because of its solubility it diffuses out of the lipid entrapment after intravenous injection. Additionally $^{17}O_2$ gas is quite expensive. Combining the perfluorocarbon gas with $^{17}O_2$ gas greatly increases the efficacy of the product and decreases the cost through more efficient use of the costly $^{17}O_2$ gas. Similarly, other gases with desirable paramagnetic properties, such as neon, may be mixed with the perfluorocarbon gases.

As Table 5, below, reveals, a wide variety of different gases may be used in MR imaging application. In Table 5, the R2 (1/T2/mmol/L.sec$^{-1}$) for different gases in gas-filled vesicles are shown. As Table 5 shows, there are dramatic differences in the relaxivity of the different gas-filled vesicles, the higher the R2 relaxation values indicating the more effective the vesicles are as MR imaging agents. Of the gases shown, air has the highest R2 value. It is believed that air is the highest because of the paramagnetic effect of the oxygen in air. Pure oxygen, however, is somewhat less effective, likely due to the higher solubility of the oxygen and equilibration of oxygen into the aqueous milieu surrounding the vesicles. With air, the nitrogen (air is about 80% nitrogen) helps to stabilize the oxygen within the vesicles. Nitrogen has much less water solubility than air. As noted above, PFP or other perfluorocarbon gases may be mixed with a more magnetically active gas such as air, oxygen, $^{17}O_2$ or rubidium enriched hyperpolarized xenon. In so doing, stable highly magnetically active gas-filled vesicles may be prepared.

TABLE 5

Size Distribution and Relaxivity

| Gas | Number Weighted Distribution (µm) | Volume Weighted Distribution (µm) | R$_2$ |
|---|---|---|---|
| Nitrogen | 6.96 ± 0.63 | 31.08 ± 7.42 | 474.6 ± 59.9 |
| Sulfur Hexafluoride | 4.31 ± 0.13 | 44.25 ± 1.23 | 319.3 ± 42.5 |
| Xenon (Rb) | 7.02 ± 1.19 | 160.90 ± 92.46 | 191.2 ± 30.8 |

TABLE 5-continued

Size Distribution and Relaxivity

| Gas | Number Weighted Distribution (µm) | Volume Weighted Distribution (µm) | R$_2$ |
|---|---|---|---|
| Argon | 8.14 ± 0.49 | 41.45 ± 13.02 | 55.29 ± 41.3 |
| Air | 6.05 ± 1.05 | 23.28 ± 0.41 | 1510.4 ± 0.41 |
| Perfluoropropane | 4.24 ± 0.72 | 49.88 ± 11.11 | 785 ± 31.8 |
| Oxygen | 7.26 ± 0.98 | 30.99 ± 3.90 | 732.4 ± 73.9 |
| Neon | 7.92 ± 0.71 | 26.20 ± 1.03 | 595.1 ± 97.2 |
| Perfluorobutane | 5.88 ± 0.36 | 51.25 ± 3.97 | 580.1 ± 45.5 |

The headspace of the container may be filled with the gas at ambient, decreased or increased pressure, as desired.

In the container of the invention, the gaseous phase is substantially separate from the aqueous suspension phase. By substantially separate, it is meant that less than about 50% of the gas is combined with the aqueous suspension phase, prior to shaking. Preferably, less than about 40%, more preferably less than about 30%, even more preferably less than about 20%, and most preferably less than about 10% of the gas is combined with the aqueous suspension phase. The gaseous phase is kept substantially separate from the aqueous suspension phase, until about the time of use, at which time the container is shaken and the gaseous phase and aqueous suspension phase combined to form an aqueous suspension of gas-filled vesicles. In this fashion, an excellent contrast agent for ultrasonic or magnetic resonance imaging is produced. Moreover, since the contrast agent is prepared immediately prior to use, shelf-life stability problems are minimized.

III. CONTAINER VOLUME AND HEADSPACE

It has been discovered that the size of the headspace of gas may also be used to affect gas-filled vesicle size. Since a larger headspace contains proportionately more gas relative to the size of the aqueous phase, large headspaces will generally produce larger vesicles than smaller sized headspaces. Therefore, the headspace, expressed as a percentage of the total volume of the vessel, should not exceed a maximum value. Moreover, too small a headspace will not allow sufficient room for the fluid to move during the shaking to efficiently form vesicles.

For example, it is a discovery of this invention that when using vials of 3.7 ml actual volume (Wheaton 300 Borosilicate glass, Wheaton Industries, Millville, N.J., referred to as 2 ml nominal size, diameter×height=15 mm×32 mm), the volume of the gas-containing headspace is preferably between about 10% and about 60% of the total volume of the vial. Generally, the gas-containing headspace in a vial is between about 10% and about 80% of the total volume of that vial, although depending upon the particular circumstances and desired application, more or less gas may be appropriate. More preferably, the headspace comprises between about 30% and about 70% of the total volume. In general, it has been found that the most preferred volume of gas-containing headspace is about 60% of the total volume of the container.

IV. OPTIMUM VALUES FOR THE SHAKING PARAMETERS

A. Shape of the Travel Path and Amplitude of Shaking

As previously discussed, in addition to the compositions of the aqueous suspension and gaseous phases, the specific manner in which the vessel containing these phases is shaken will affect the vesicle size distribution. The optimal shaking conditions can be defined by reference to four parameters—the shape of the path traveled by the container during the shaking, the amplitude of the shaking motion, the frequency of the shaking, and the duration of the shaking.

It has been found that the path traveled by the container during the shaking is especially significant in the formation of proper sized vesicles. In particular, it has been found that small vesicles can be produced in a minimum amount of time when the shaking takes the form of reciprocal motion. Other types of shaking, such as vortexing, can also produce small vesicles. However, reciprocal shaking greatly reduces the duration of the shaking that is necessary to achieve a high concentration of small vesicles.

The inventors have found that vesicles of small size are obtained in a relatively short period of time—i.e., 2 minutes or less—when the shaking amplitude—specifically, the length C of the reciprocal path traveled by the container during the shaking—is at least 0.3 cm. In general, the larger the amplitude of the shaking, the smaller the vesicles. However, as discussed below, the frequency of the shaking is also an important parameter. Since practical considerations associated with the shaking equipment will typically result in a drop in shaking frequency to undesirably low levels when the shaking amplitude is increased beyond a certain maximum amount, the amplitude should be maintained sufficiently low to ensure that the shaking frequency remains adequate. For the Wig-L-Bug™ model 3110B shaking device, this maximum amplitude is approximately 2.5 cm.

Figure 3:
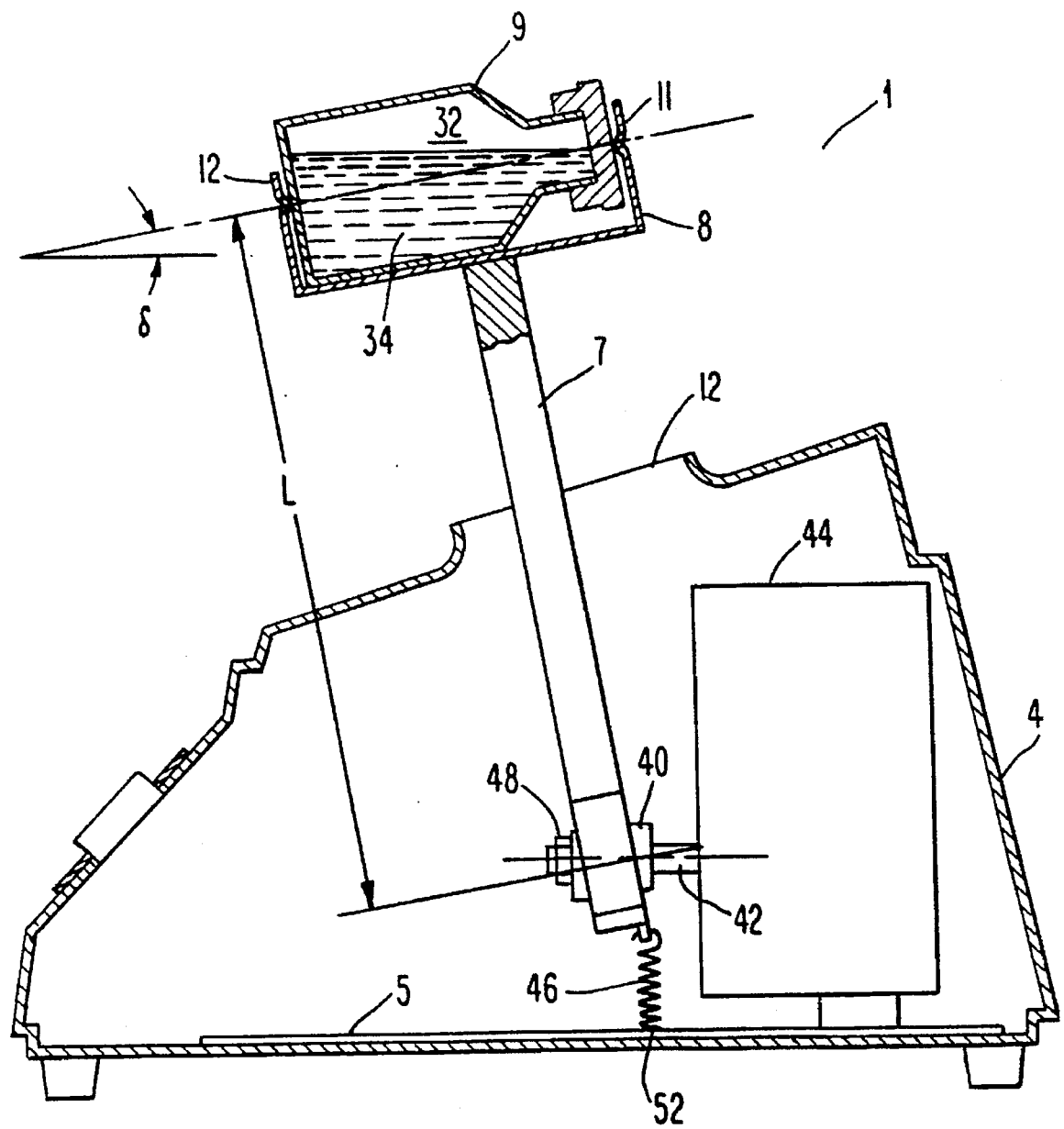
FIG. 3 is a longitudinal cross-section through the shaking apparatus shown in FIG. 2, without the cover, but including the installation of the container shown in FIG. 1.
Figure 4:
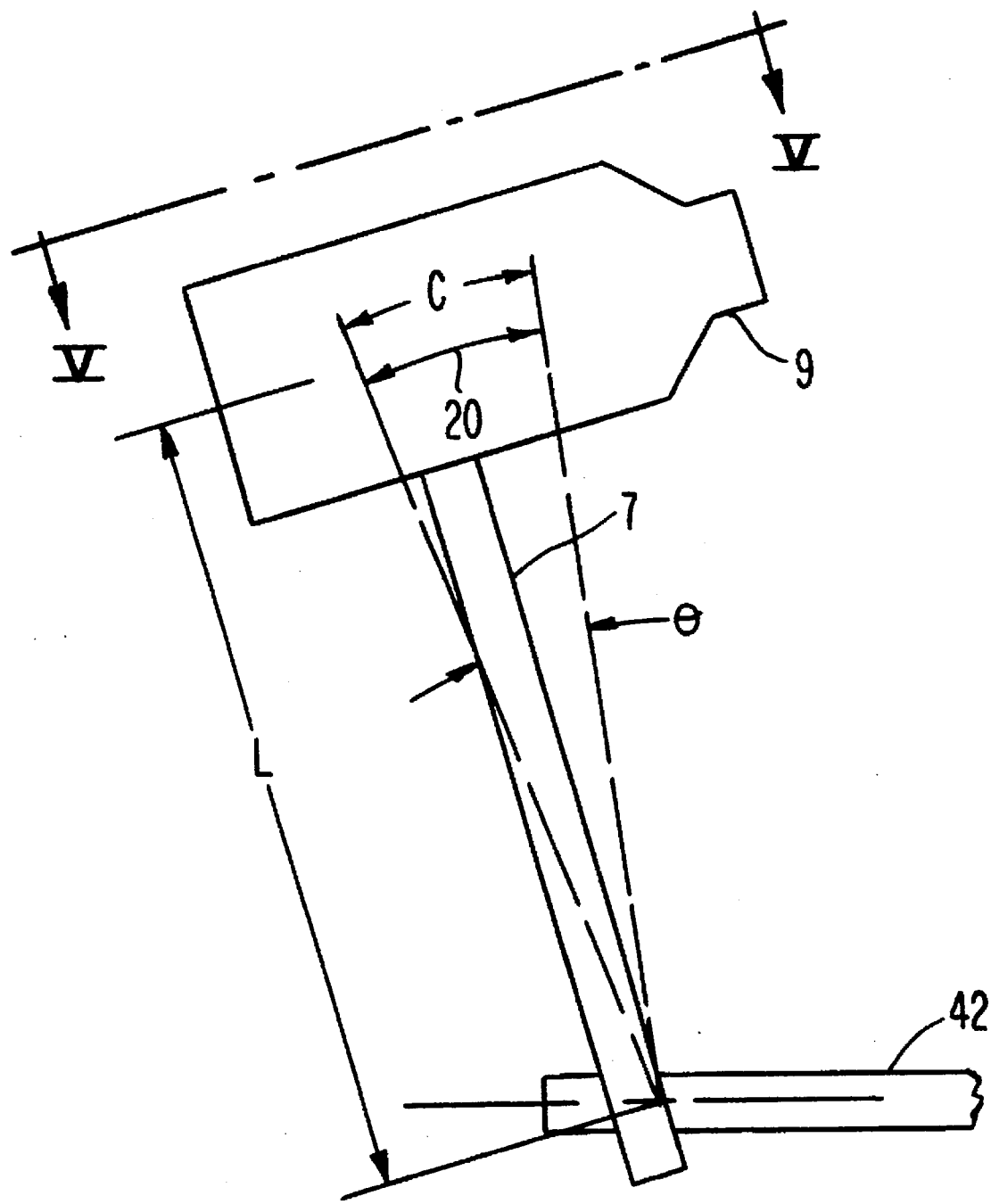
FIGS. 4 and 5 are elevation and plan views, respectively, of the path taken by the container shown in FIG. 1 when it is installed on the shaking apparatus shown in FIG. 2, with FIG. 5 being taken along the line V—V shown in FIG. 4.

The inventors have also found that it is preferable that the reciprocal motion occur along an arcuate path 20, as shown in FIG. 4, wherein the amplitude of the shaking motion is denoted C, since high frequency shaking motion is more readily accomplished in this manner. In the preferred embodiment of the invention, the arcuate path 20 is defined by a radius of curvature L, which is formed by a shaker arm of length L. Preferably, the shaker arm 7 has a length L of at least 6 cm and rotates through an angle θ of at least 3°. As discussed further below, according to the preferred embodiment of the invention, the angle of rotation of the shaker arm θ is achieved by employing a bearing having an offset angle equal to θ. Further, the length L of the shaker arm is defined as the distance from the center line of an eccentric bushing 40 on which the shaker arm 7 bearing 50 is mounted, as discussed further below, to the centerline of the container 9, as shown in FIG. 3.

The use of longer shaker arm lengths L and larger angles of rotation θ will increase the amplitude of the shaking and, therefore, will generally reduce vesicle size. However, as discussed above, the maximum values for the shaker arm length L and the angle of rotation θ employed should be limited to ensure that the amplitude of shaking C does not become so large that an inadequate shaking frequency results. In addition, mechanical considerations will also limit the size of the angle of rotation of the shaker arm 7. For the Wig-L-Bug™ model 3110B, the maximum shaker arm length and angle of rotation that should be employed are approximately 15 cm and approximately 9°, respectively.

Additionally, it is preferred that the shaking device superimpose a reciprocal motion in a second, approximately perpendicular, direction onto the reciprocal motion in the first direction. Preferably, the amplitude of shaking in the second direction C' is at least approximately one tenth that of the amplitude of shaking in the first direction C. For purposes of description, the first direction of reciprocating motion will be referred to as the longitudinal direction and the second direction of reciprocating motion will be referred to as the transverse direction.

Figure 8:
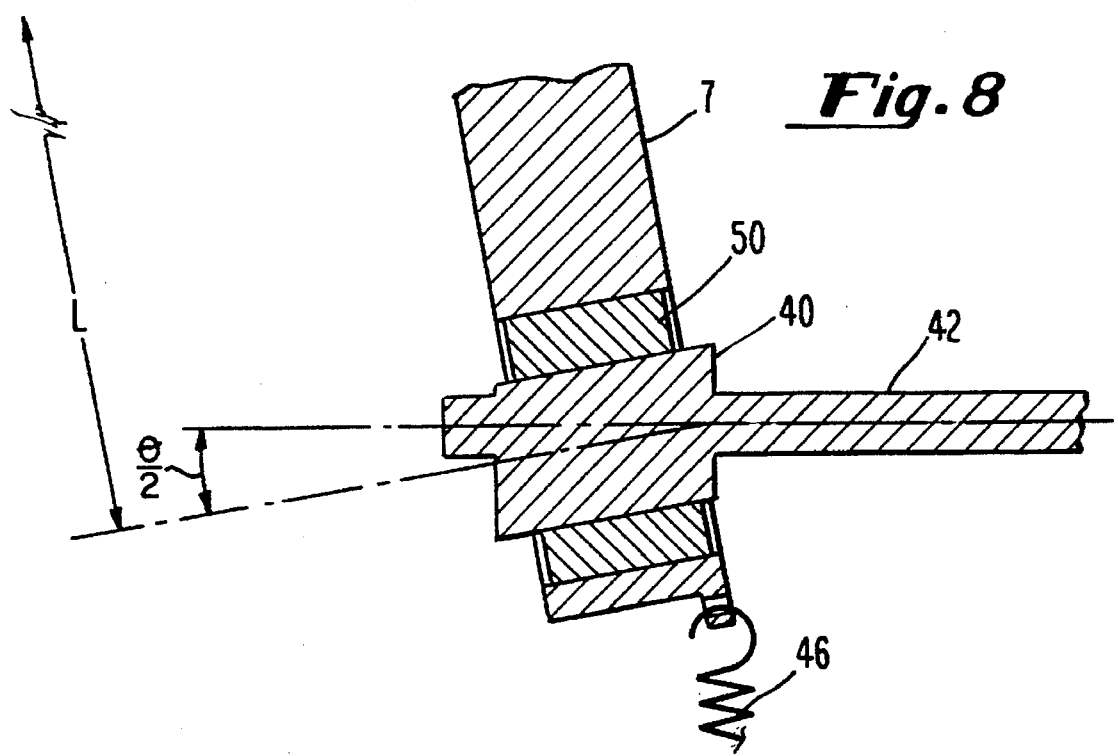

Optimally, the timing of the motions in the longitudinal and transverse directions are adjusted so that the summation of the motions in the two directions results in the container 9 shaking in a figure-8 pattern.

Figure 5:
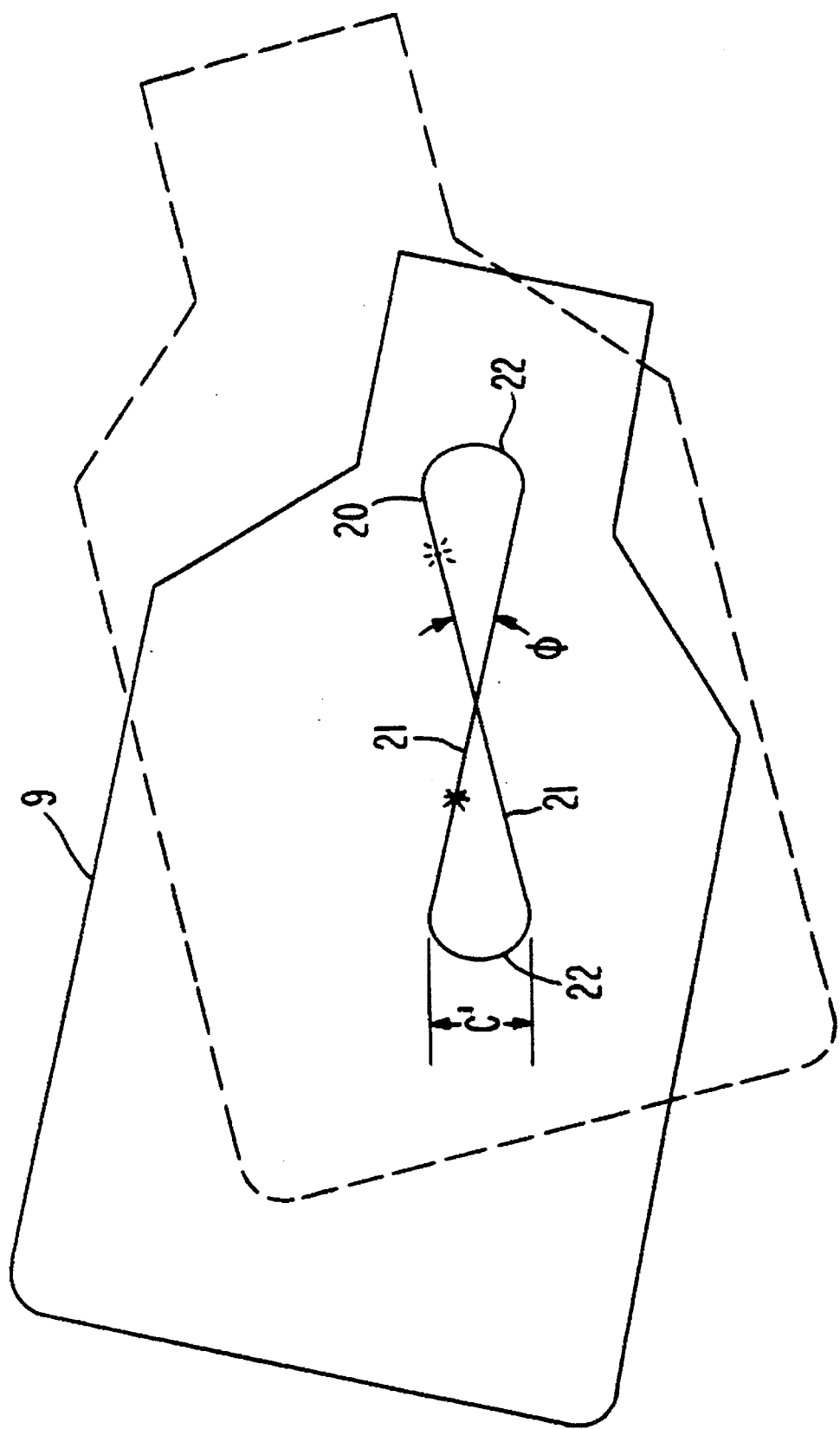

Based on the foregoing, the preferred shaking path 20 described by the container 9 when attached to the end of the shaker arm 7 of the shaking device 1 of the current invention is shown in FIGS. 4 and 5. As shown in FIG. 5, according to the current invention, the shaker arm 7 imparts motion to the container 9 in the transverse direction as it move back and forth in the longitudinal direction in such a way that a point on the container 9 travels in a figure-8 pattern 20. The length of the figure-8 is the amplitude in the longitudinal direction C and the width of the figure-8 is the amplitude of the shaking in the transverse direction C'. When viewed from the side, as shown in FIG. 4, the path is arcuate in the longitudinal direction—specifically, an arc having a radius of curvature that is equal to the length L of the shaker arm 7. The arc length C is the product of the shaker arm length L and the angle θ encompassed by the shaker arm rotation in the longitudinal plane, expressed in radians—that is, $C=L\theta$.

Figure 9A:
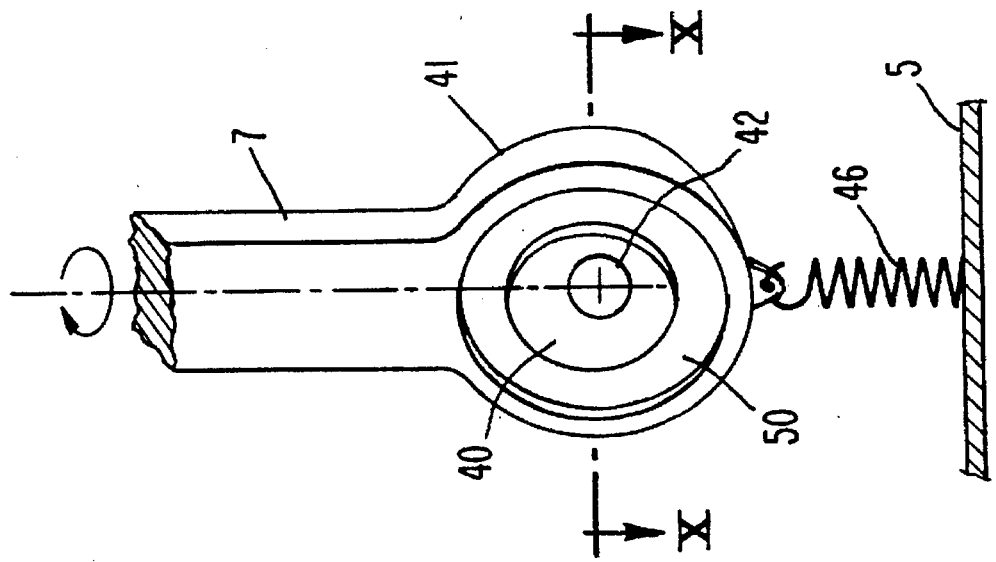
FIGS. 9(a) and 9(b) are views taken along line IX—IX shown in FIG. 7 of the shaker arm, except that in FIGS. 9(a) and (b) the eccentric bushing has been rotated 90° and 270°, respectively, from its orientation shown in FIG. 7.
Figure 9B:
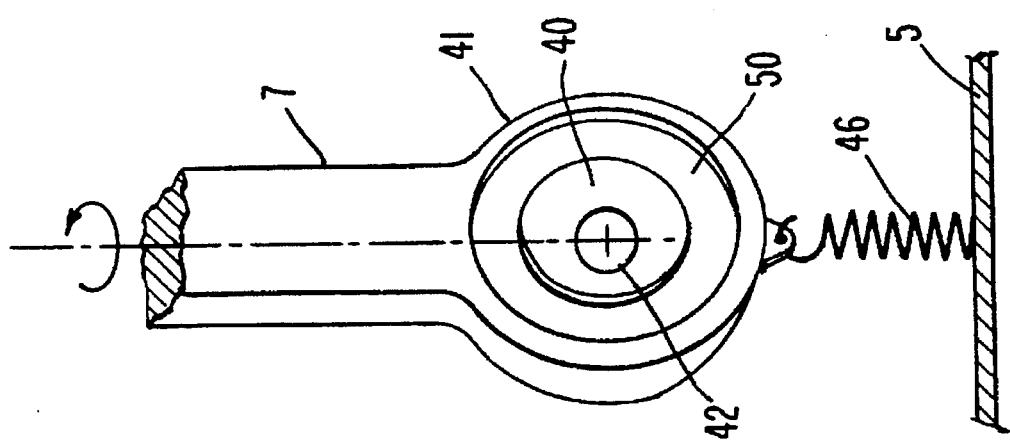
Figure 10:
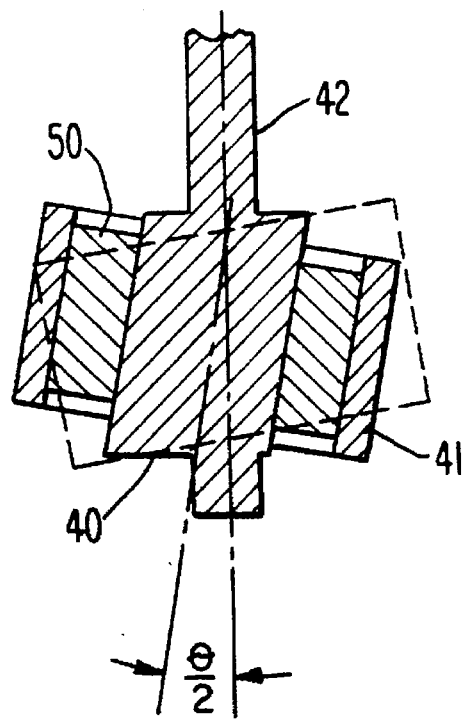
FIG. 10 is a cross-section taken through line X—X shown in FIG. 9(b), with the orientation of the sleeve when the eccentric bushing has been rotated 180° shown in phantom.
Figure 12:
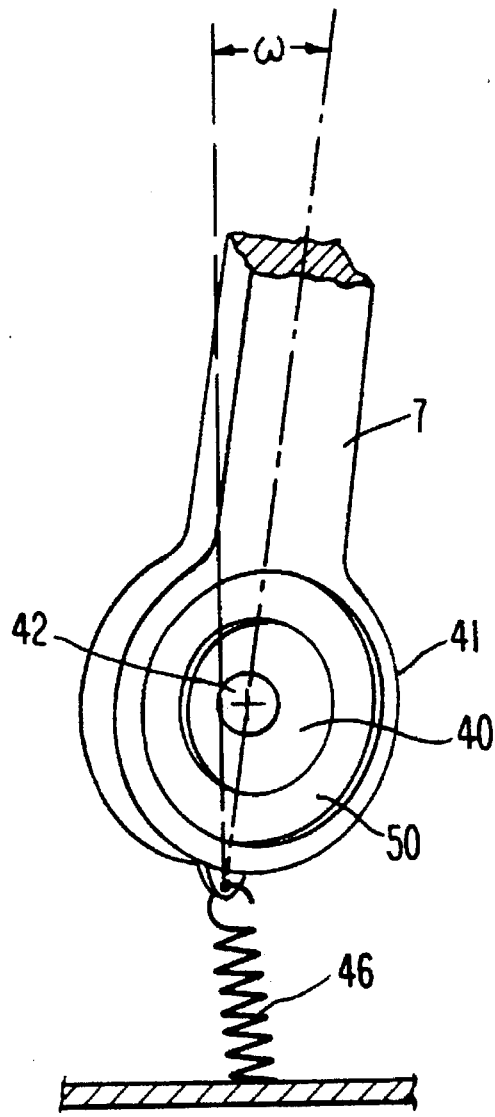
FIG. 12 is a view similar to FIG. 9 showing the orientation of the shaker arm when lower spring tension is employed.

Preferably, the figure-8 pattern is comprised of approximately two straight sections 21 that intersect at an angle $\phi$ and two approximately half-circle sections 22. As discussed further below, in the preferred embodiment of the invention, the angle $\phi$ formed by the figure-8 pattern is approximately equal to the angle of rotation of the shaker arm 7 in the longitudinal direction θ. As discussed below, this is accomplished by applying sufficient force to the shaker arm 7 from a spring 46 so as to maintain the shaker arm essentially in a vertical orientation in the transverse plane during the shaking, as shown in FIGS. 9 and 10. If the spring tension is adjusted to permit the shaker arm 7 to rotate through an angle in the transverse plane ω, as shown in FIG. 12, then the angle θ of the figure-8 shaking pattern experienced by the container 9 will be greater than θ.

If $\phi$ equals θ, then the total distance D traveled in one circuit around the path 20 will be a function of two variables—the length of the shaker arm L and the angle θ described by the shaker arm as it travels in the longitudinal plane. This distance D can be approximated by the equation:

$$D=2L[(2 \sin \theta/2 + \Pi \tan^2\theta/2)/(1+\tan \theta/2)].$$

Since, preferably, the length L ms at least 6 cm and the angle θ is at least 3°, the distance D should preferably be at least about 0.6 cm.

Further, given that $\phi=\theta$, the amplitude of shaking in the transverse direction C' will be a function of the amplitude in the longitudinal direction C and the angle θ, and can be approximated by the equation:

$$C'=(2C\tan \theta/2)/(1+\tan \theta/2)$$

Since, preferably, the amplitude of the shaking in the longitudinal direction C is at least about 0.3 cm and the angle θ is at least about 3°, the amplitude in the transverse direction C' should preferably be at least about 0.02 cm.

The optimum values for the amplitude and shape of the shaking motion discussed above were arrived at based on a series of tests, discussed below in sub-section C.

B. Frequency and Duration of Shaking

In addition to the shape and amplitude of the shaking motion, the frequency of the shaking is also an important parameter in forming proper sized vesicles. The shaking frequency is quantified in terms of the revolutions per minute ("RPM") experienced by the shaker arm 7 and is defined as the number of times the shaker arm, and, therefore the container 9 attached to it, traverses the entirety of the shaking path in one minute. Thus, in the preferred embodiment of the invention, shaking at a frequency of 3600 RPM means that the container 9 undergoes shaking motion around the figure-8 path 20 thirty six hundred times in one minute, or sixty times in one second.

It has been found that vesicles can be made using shaking frequencies in the range of 100 RPM to 10,000 RPM. However, it has been found that there is a minimum shaking frequency that will result in the production of optimally sized vesicles within a relatively short period of time. As discussed in section C, below, in has been found that this minimum frequency is approximately 2800 RPM. Although, in general, increasing the shaking frequency will reduce vesicle size, the limitations of the shaking device will typically set the maximum obtainable frequency. For the Wig-L-Bug™, the maximum obtainable frequency is about 3300 RPM.

At frequencies in the range of 2800 to 3300 RPM, the optimum duration of the shaking is at least approximately 60 seconds. However, the optimal duration of the shaking is related to the frequency and may be lower at higher frequencies. Thus, for example, at 4500 RPM the optimal duration of the shaking is only 50 seconds.

C. Test Results

The optimum value for the shaking frequency, as well as the shape and amplitude of the shaking motion, were developed through a series of tests, as discussed below.

A first series of tests were conducted to determine the effect of shaking frequency on vesicle size. One mg mL$^{-1}$ samples of lipid consisting of dipalmitoylphosphatidylcholine (DPPC) (Avanti Polar Lipids, Alabaster, Ala.), dipalmitoylphosphatidic acid (DPPA) (Avanti Polar Lipids, Alabaster, Ala.), and dipalmitoylphosphatidylethanolamine covalently bound to polyethyleneglycol monomethyl ether of molecular weight=5000, (DPPE PEG-5000) (Avanti Polar Lipids, Alabaster, Ala.), in a mole ratio of 82 mole %: 10 mole %: 8 mole % respectively, were added to a diluent consisting of normal saline, glycerol (Spectrum Chemical Co., Gardena, Calif.), and propylene glycol (Spectrum Chemical Co., Garden, Calif.), (8:1:1, v:v:v). The samples were then heated to 45° C. for 10 minutes then allowed to equilibrate to room temperature (25° C.).

The samples were then added to nominal 2.0 mL borosilicate vials (VWR Scientific, Boston, Mass.) of the type shown in FIG. 1 (actual volume 3.7 mL). The vials were then sealed with a butyl rubber stopper and closed to a gas-tight fit with an aluminum crimp. The headspace in the vials was approximately 60% of the total volume of the vials. Samples were then purged with perfluoropropane (Flura Corporation, Nashville, Tenn.) and placed on the shaking device shown in FIG. 3, which is discussed further in section V.

The containers were shaken for 2 minutes using the figure-8 type motion shown in FIGS. 4 and 5. The length of the shaker arm L was 7.7 cm and the bearing offset angle θ and, therefore, the angle of rotation of the shaker arm in the longitudinal plane, was 6°. Using the relationships discussed above, it was determined that the amplitude of shaking in the longitudinal and transverse directions C and C' were approximately 0.8 cm and 0.1 cm, respectively. Shaking frequencies of 1500, 2800 and 3300 RPM were used, measured via a Code-Palmer Model 08210 Pistol Grip tachometer (Code-Palmer, Nile, Ill.). Sizing was determined by small particle optical sizing on a Particle Sizing System light obscuration particle sizer (Santa Barbara, Calif.).

Table 6 shows the results of these tests and demonstrates the effect that shaking frequency has on the resultant average vesicle size.

TABLE 6

Effect of Shaking Frequency on Average Vesicle Size

| Frequency (RPM) | Average Vesicle Size |
|---|---|
| 1500 | 3.4 μm |
| 2800 | 3.3 μm |
| 3300 | 2.9 μm |

As can be seen, shaking at a frequency in excess of 2800 RPM greatly reduces the average vesicle size obtained after 2 minutes of shaking.

A second set of tests were conducted to determine the effect on vesicle size of increasing the shaker arm length L, and, therefore, the shaking amplitude in the longitudinal and transverse directions C and C', as well as the shaking distance per cycle D. The tests were conducted the same as those discussed above except that the containers were shaken for 60 seconds using shaker arm lengths L over the range of 6.7 to 14.8 cm.

Figure 13:
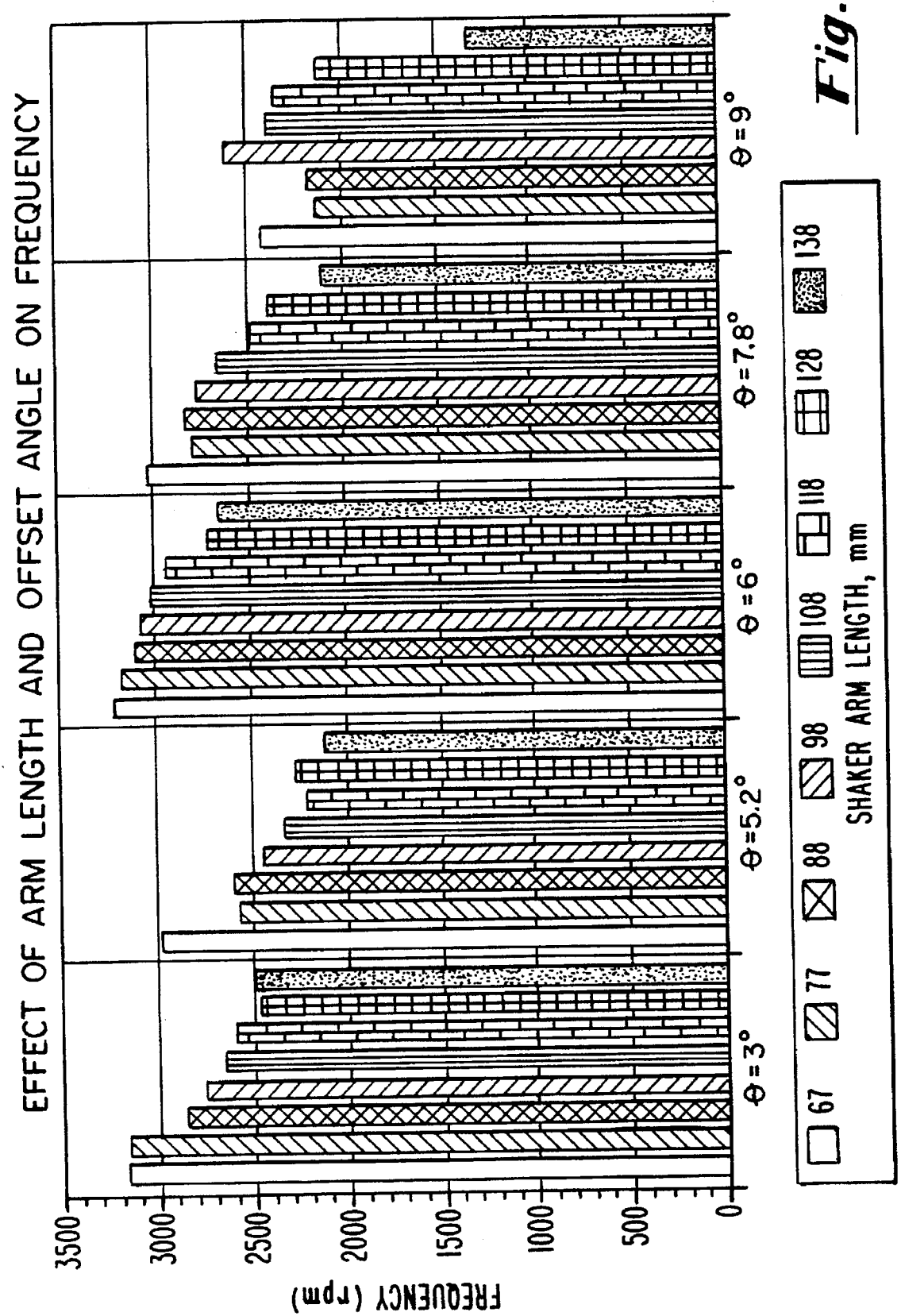
FIG. 13 is a chart showing the relationship between the shaking frequency, in RPM, on the one hand, and the shaker arm length L, in cm, and bearing offset angle θ, on the other hand, used to obtain the test results shown in FIGS. 14–16.

The variations in the shaker arm length resulted in variations in shaking frequency over the range of 2250 to 3260 RPM, with the shaking frequency decreasing as the shaker arm length increased. The variation in shaking frequency with the shaker arm length L and the shaker arm rotation angle θ is shown in FIG. 13. Thus, for example, when a shaker arm length L of 6.7 cm and an angle of rotation θ of 6° were used, the frequency of shaking was approximately 3200 RPM, whereas when the shaker arm length was increased to 13.8 cm, while maintaining the same angle of rotation, the frequency dropped to about 2700 RPM.

Figure 14A:
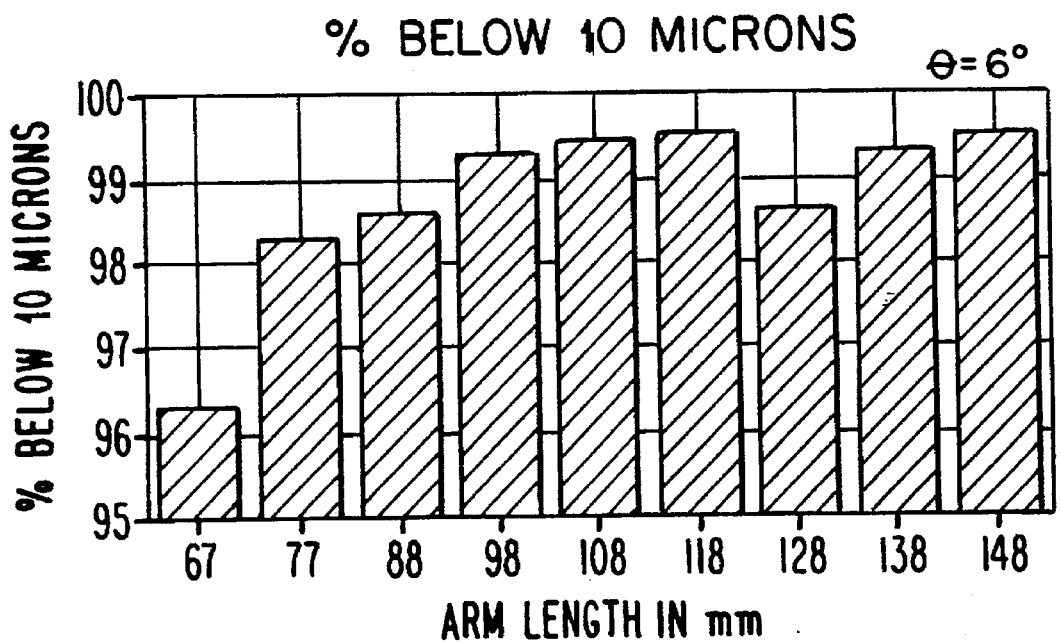
FIGS. 14(a) through 14(c) are charts showing the percentage of the vesicles having a size less than 10 μm, the number weighted mean size, and the particles per mL, versus the shaker arm length L, in mm, as the shaker arm length and RPM are varied in accordance with FIG. 13, at a bearing offset angle θ of 6°.
Figure 14B:
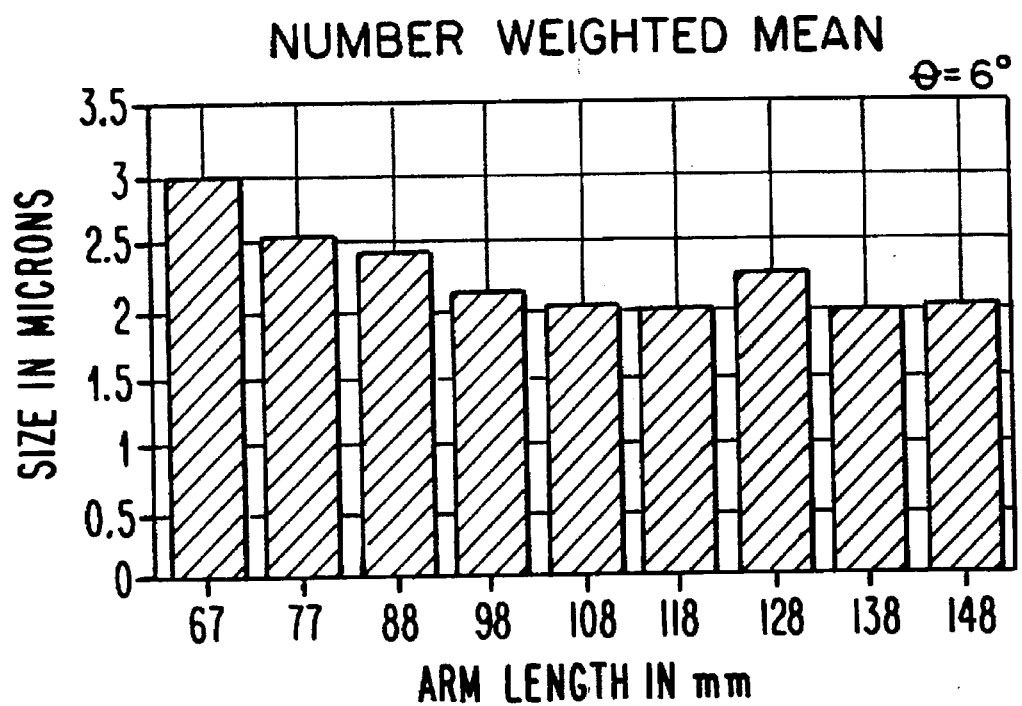
Figure 14C:
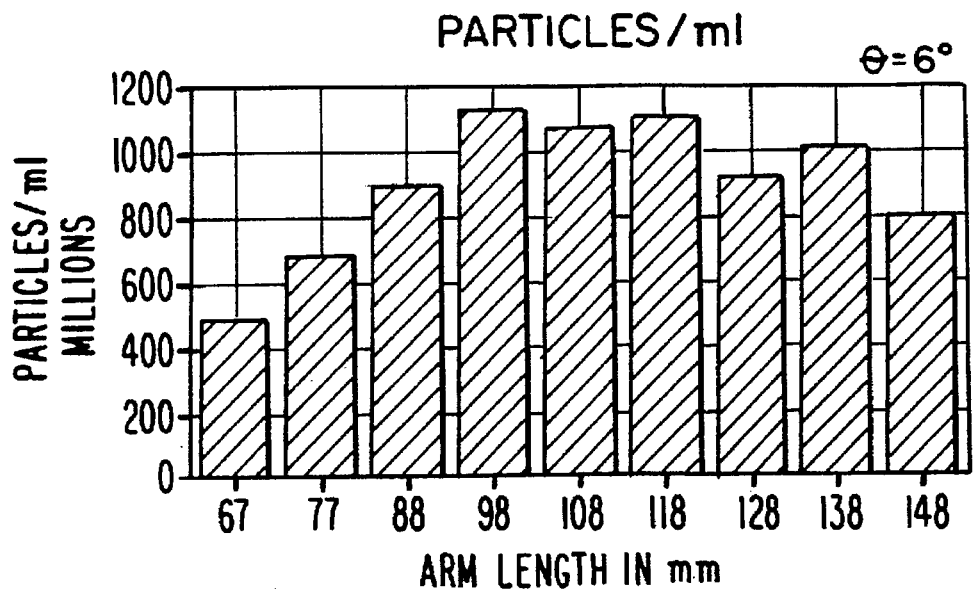

The results of this series of tests are shown in FIGS. 14(a)–(c). As shown in FIG. 14(a), with a angle of rotation in the longitudinal plane θ of 6°, at least 98% of the vesicles are below 10 microns whenever the shaker arm length L is 7.7 cm or greater—that is, when the amplitudes of shaking in the longitudinal direction C is greater than 0.8 cm. Moreover, the percentage of vesicles below 10 μm reaches a plateau of about 99 to 99.5% at shaker arm lengths L of 9.8 cm and above—that is, when the amplitudes of shaking in the longitudinal direction is 1.0 cm and above. The number weighted mean size of the vesicles reaches a plateau of about 2 μm at these same conditions, as shown in FIG. 14(b).

Although the general effect of increasing shaking frequency is to reduce vesicle size when all other variables are held constant, as previously discussed and shown in Table 6, these data show that increasing the shaking amplitude by increasing the shaker arm length reduces the size of the vesicles even when such increases are combined with reductions in shaking frequency, as shown in FIG. 13.

As shown in FIG. 14(c), more than 400×10$^6$ vesicle per mL were obtained at all shaker arm lengths and, in fact, the use of shaker arm lengths in the range of about 10 to 12 cm resulted in the production of more than 1000×10$^6$ vesicle per mL. However, as the shaker arm length is increased above about 12 cm, the particles per mL began dropping and reached 800×10$^6$ vesicles per mL at 14.8 cm. Although not shown in FIG. 13, with a 14.8 cm shaker arm length and a 6° shaker arm angle of rotation, the frequency was determined to be only 2550 RPM. Thus, the drop in the concentration of vesicles produced with a 14.8 cm arm length is thought to be due to the drop in shaking frequency that accompanies increases in shaking amplitude, as previously discussed. Therefore, these data indicate that when using a Wig-L-Bug™ shaking device, the shaker arm length should preferably be less than approximately 15 cm to maximize vesicle concentration.

A third series of tests were performed using the same materials and procedure discussed above except that the bearing offset angle and, therefore, the angle of the shaker arm rotation in the longitudinal direction θ, was increased from 6° to 9°, thereby increasing the amplitude of shaking in the longitudinal direction. In addition, shaker arm lengths in excess of 11.8 cm were not used. The results of these tests are shown in FIGS. 15(a)–(c), along with the results of the previously discussed set of tests for comparison.

Figure 15A:
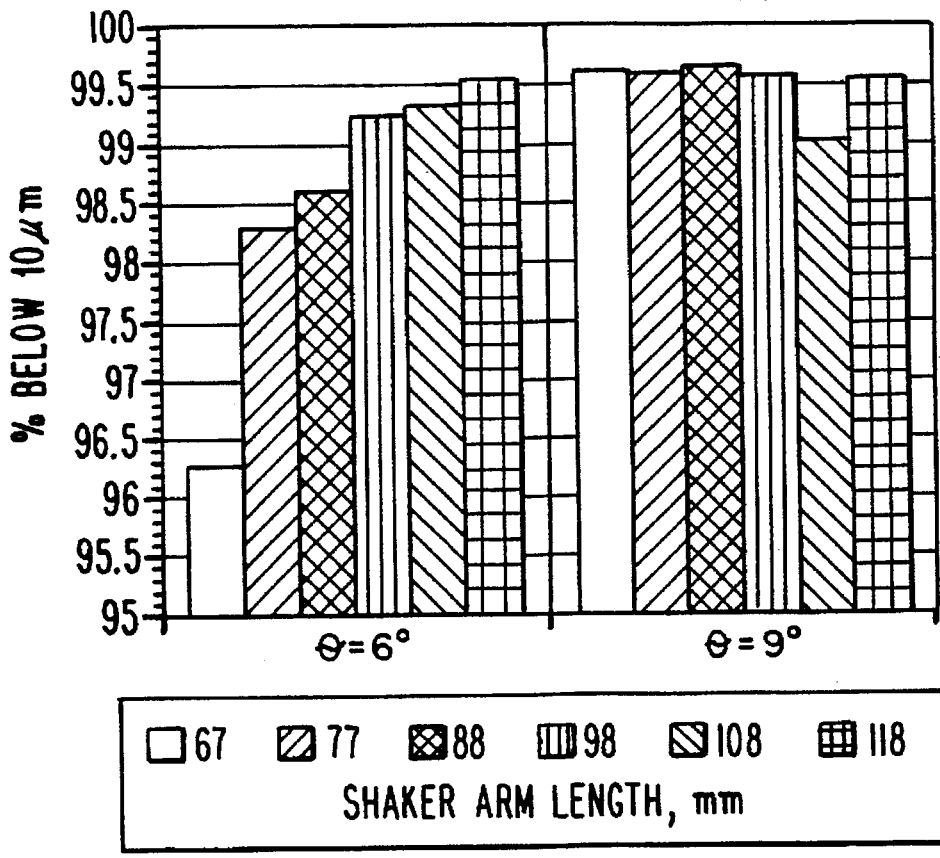
FIGS. 15(a) through 15(c) are charts similar to FIGS. 14(a)–14(c) comparing the results obtained using a bearing offset angle θ of 9° to those shown in FIGS. 14(a)–(c).
Figure 15B:
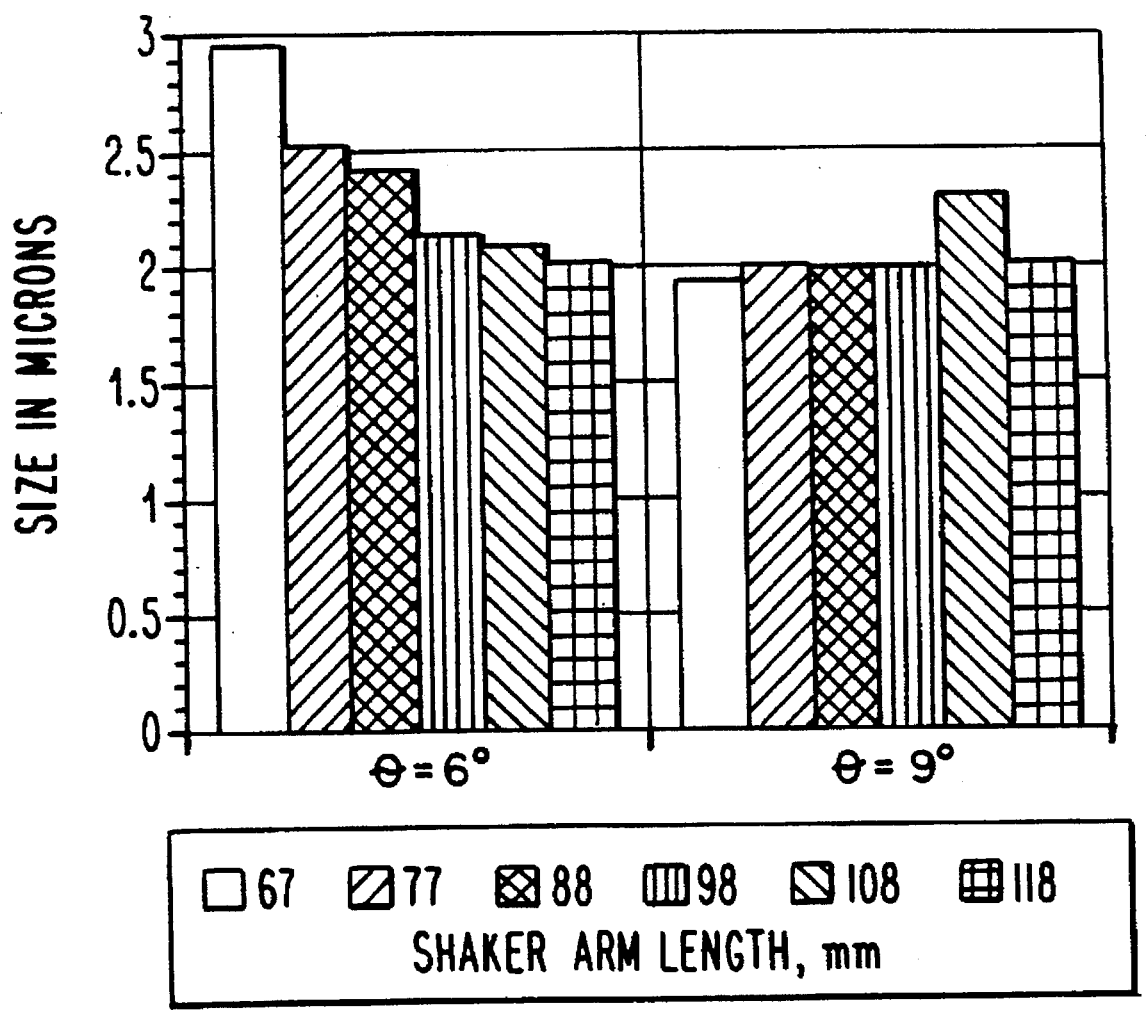
Figure 15C:
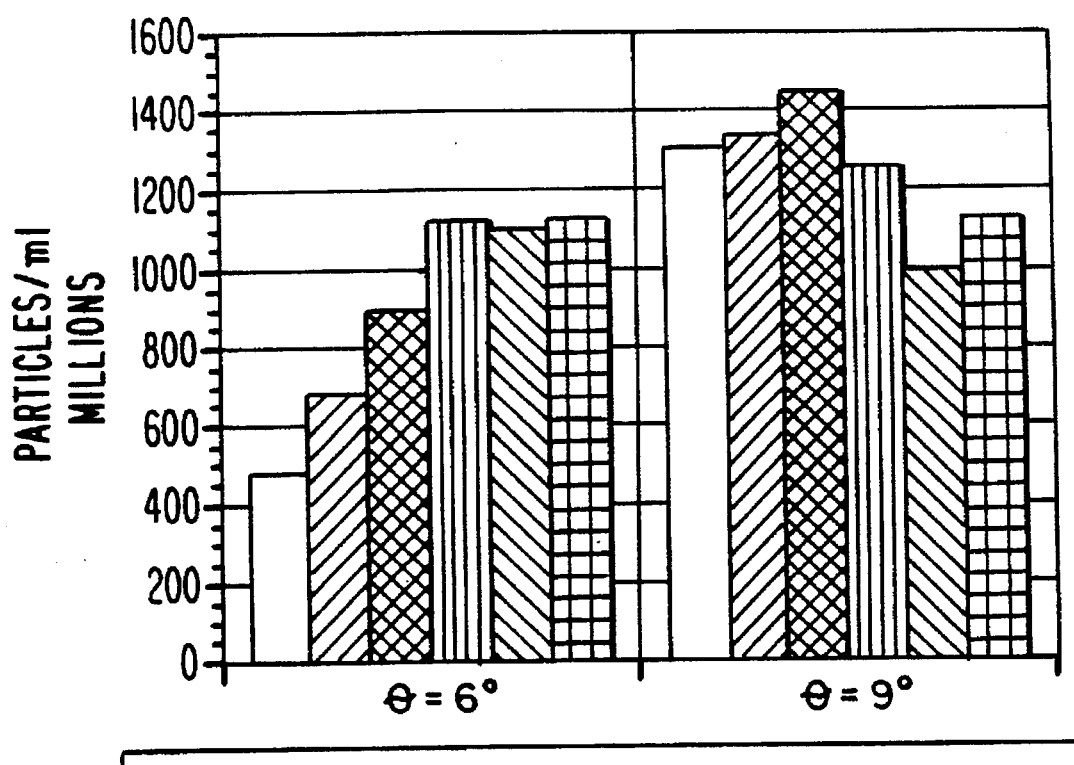

As can be seen in FIG. 15(a), increasing the angle of rotation of the shaker arm θ from 6° to 9° reduces vesicle size, even though it also has the effect of reducing the shaking frequency, as shown in FIG. 13. Thus, with a 9° shaker arm angle of rotation, even a shaker arm length of only 6.7 cm results in over 99.5% of the vesicles being below 10 μm and a mean size of about 2 μm. In addition, in excess of $1000 \times 10^6$ vesicle per mL were obtained at all shaker arm lengths, as shown in FIG. 15(c).

Figure 16A:
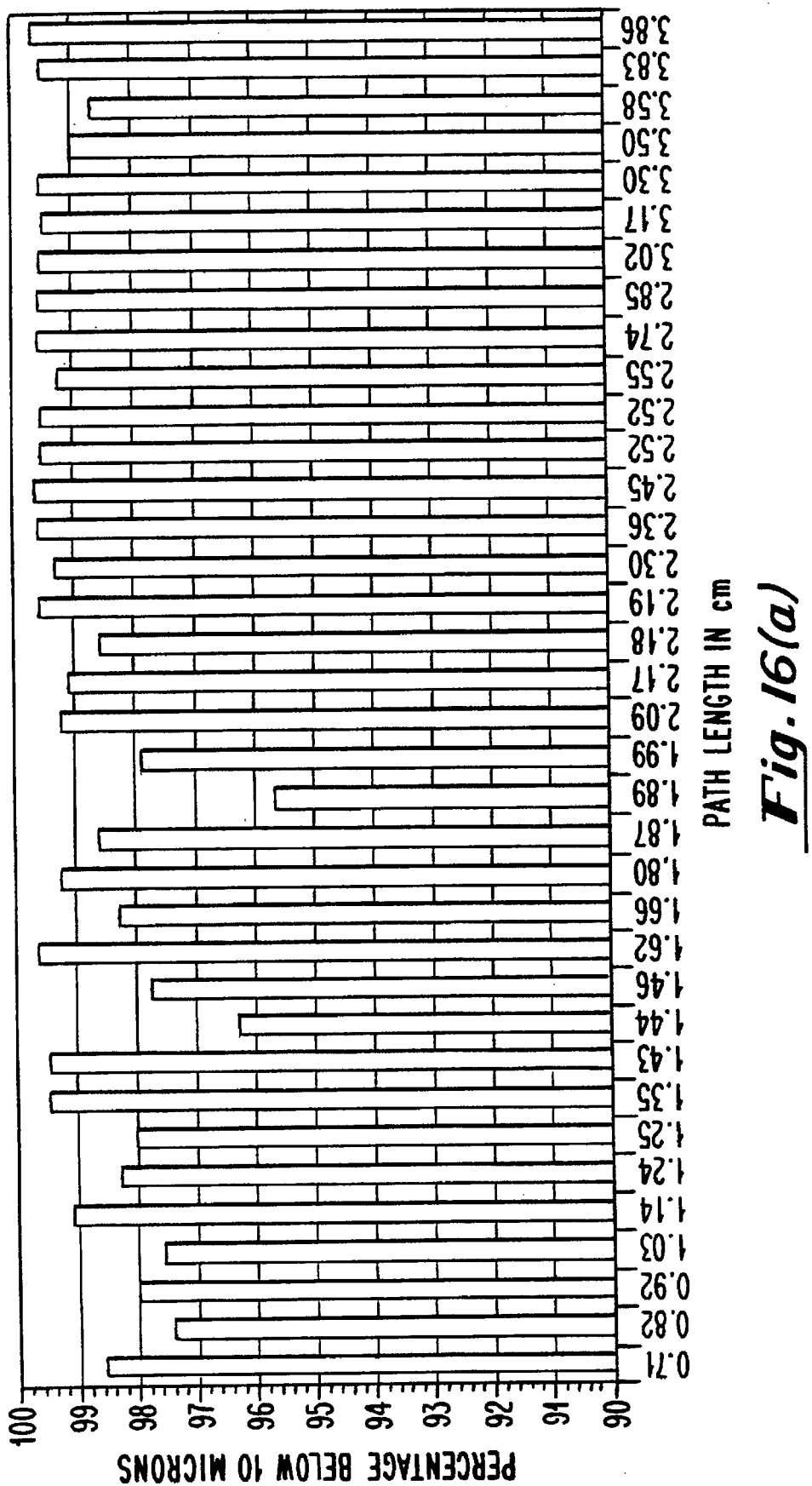
FIGS. 16(a) through 16(c) are charts showing the percentage of the vesicles having a size less than 10 μm, the number weighted mean size, and the particles per mL, versus the total length of the shaking path, in cm.
Figure 16B:
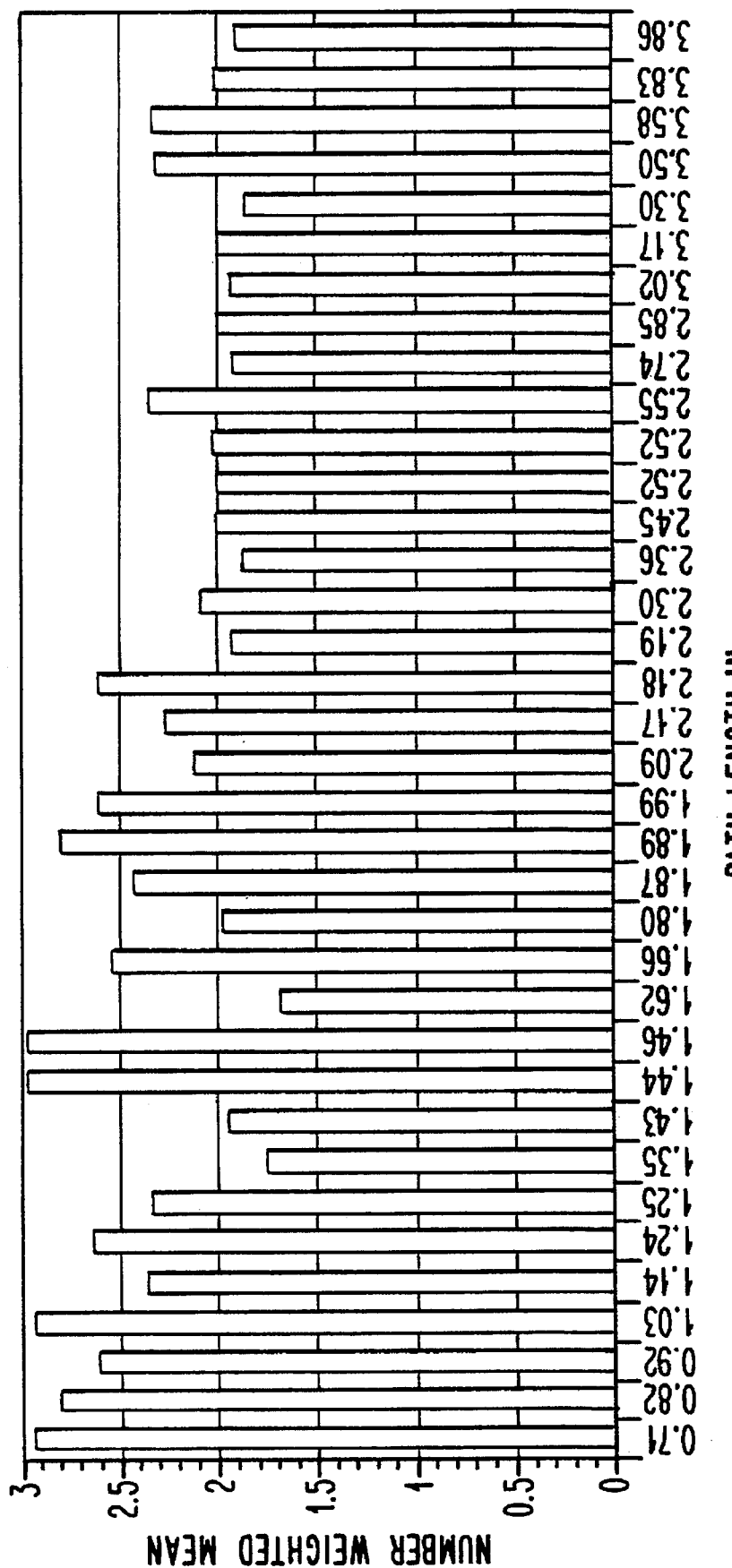
Figure 16C:
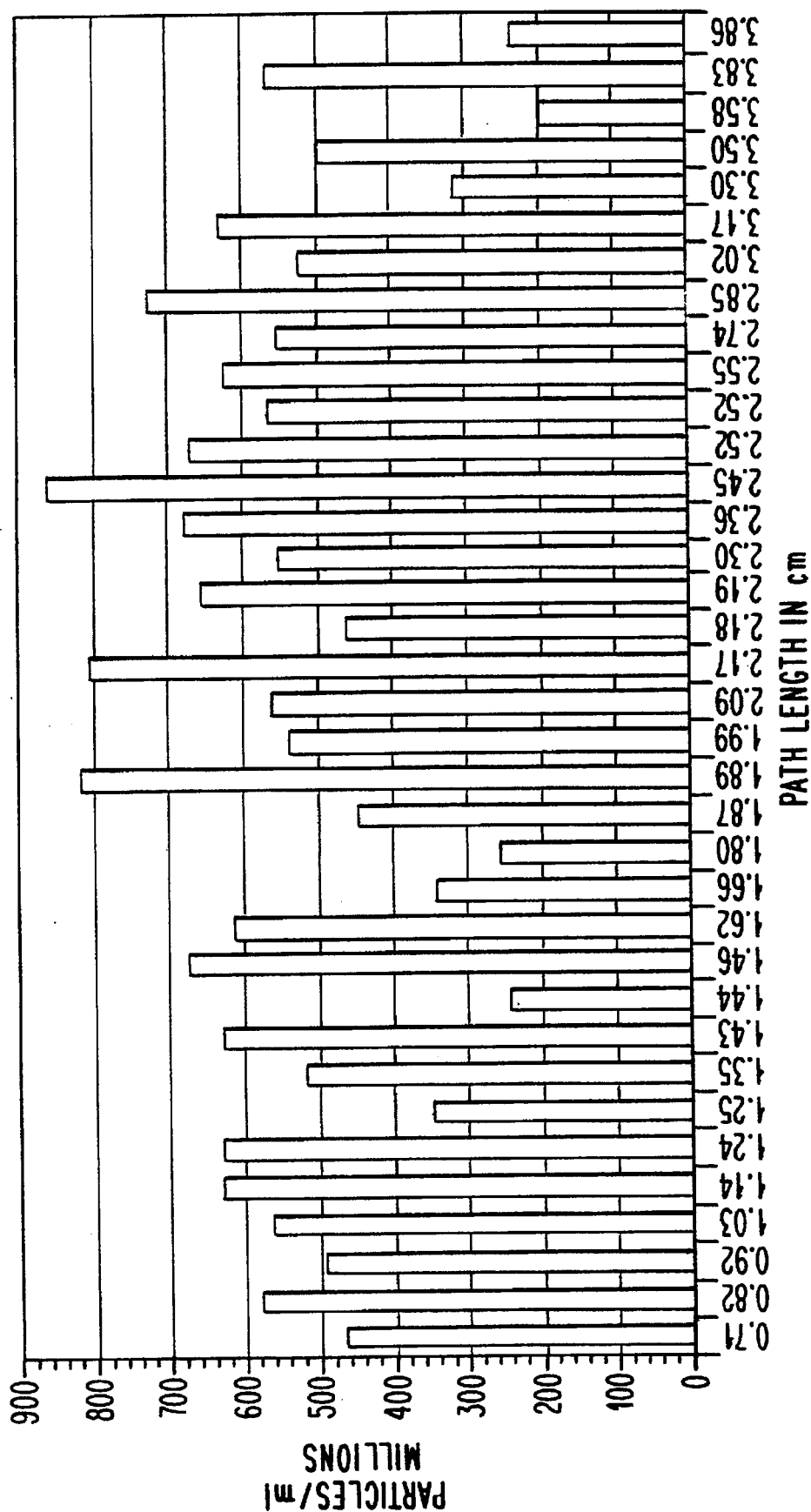
Figure 17:
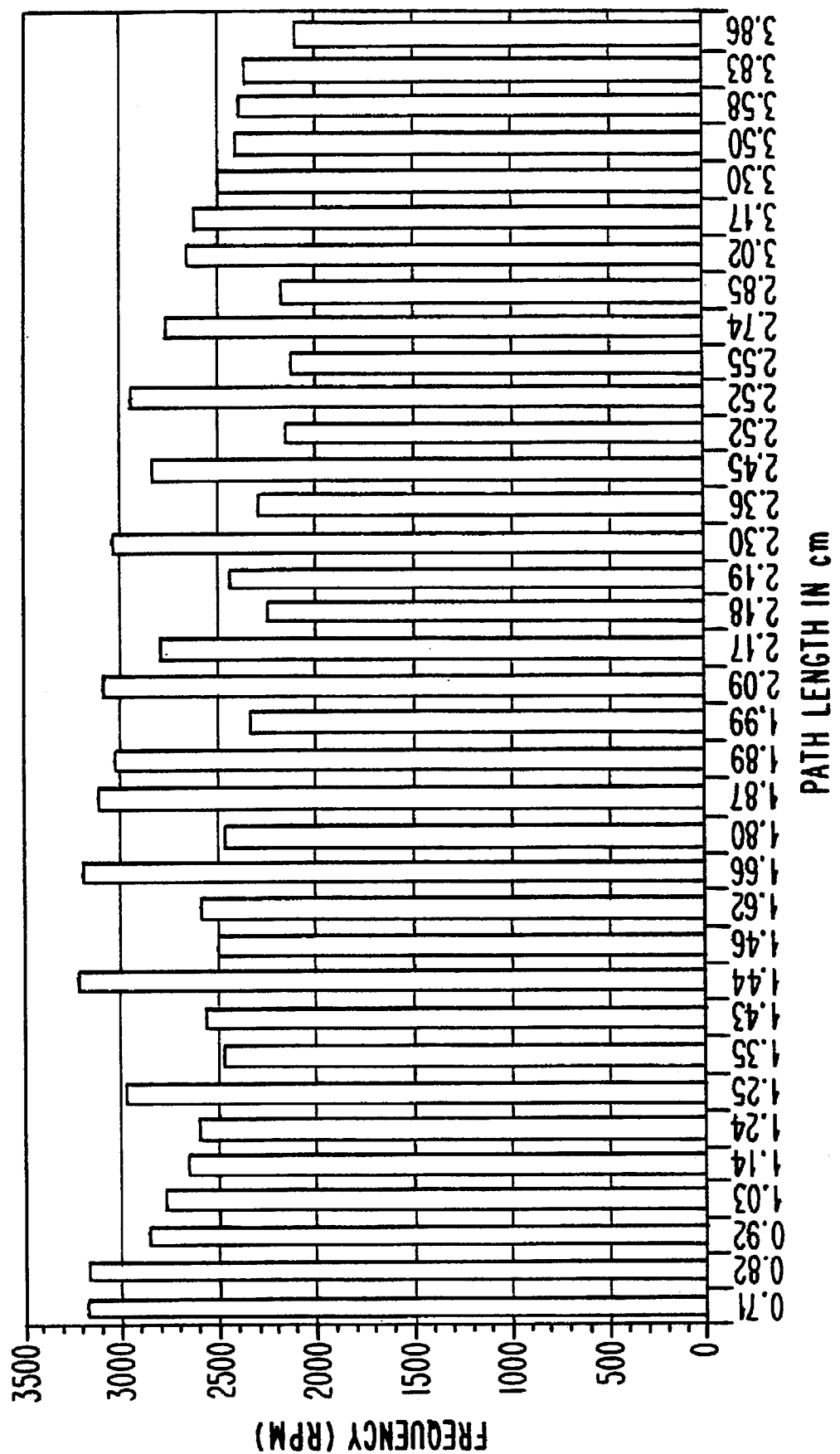
FIG. 17 is a chart showing the relationship between the shaking frequency, in RPM, and the total length of the shaking path, in cm, used to obtain the test results shown in FIG. 16.

Another series of tests were performed using the same materials and procedure discussed above except that bearing offset angles and, therefore, angles of the shaker arm rotation in the longitudinal direction θ, of 3°, 5.2°, 6°, 7.8°, and 9° were used along with shaker arm lengths L between 6.7 cm and 13.8 cm (increasing in approximately 1 cm increments). The total length D of the shaking path 20 was estimated at each point. The frequency as a function of total path length is shown in FIG. 17. The results are shown in FIGS. 16(a)–(c) as a function of the total path length D. As can be seen, under all of the conditions tested—i.e., at total path lengths D of 0.7 cm and above—more than 95% of the vesicles were less than 10 μm and the concentration of vesicles produced was more than $100 \times 10^6$ per mL. Further, under all conditions in which the total path length D was 2.19 cm or greater, more than 98% of the vesicles were less than 10 μm. This suggests that the total path length of the shaking motion should be at least 0.7 cm and, more preferably, at least 2.2 cm.

Thus, the foregoing shows that vesicles of small size can be obtained in about two minutes or less when reciprocal shaking is conducted such that the frequency of shaking is at least approximately 2800 RPM. In addition, the shaking motion should be accomplished in two substantially perpendicular directions, and, more preferably, in a figure-8 pattern. Further, the amplitude of shaking in the major direction should be at least 0.3 cm and, more preferably at least 0.8 cm, or the total length of the shaking path should be at least 0.7 cm and, more preferably, at least 2.2 cm.

V. THE APPARATUS OF THE INVENTION

A. THE PREFERRED SHAKING DEVICE

Figure 2:
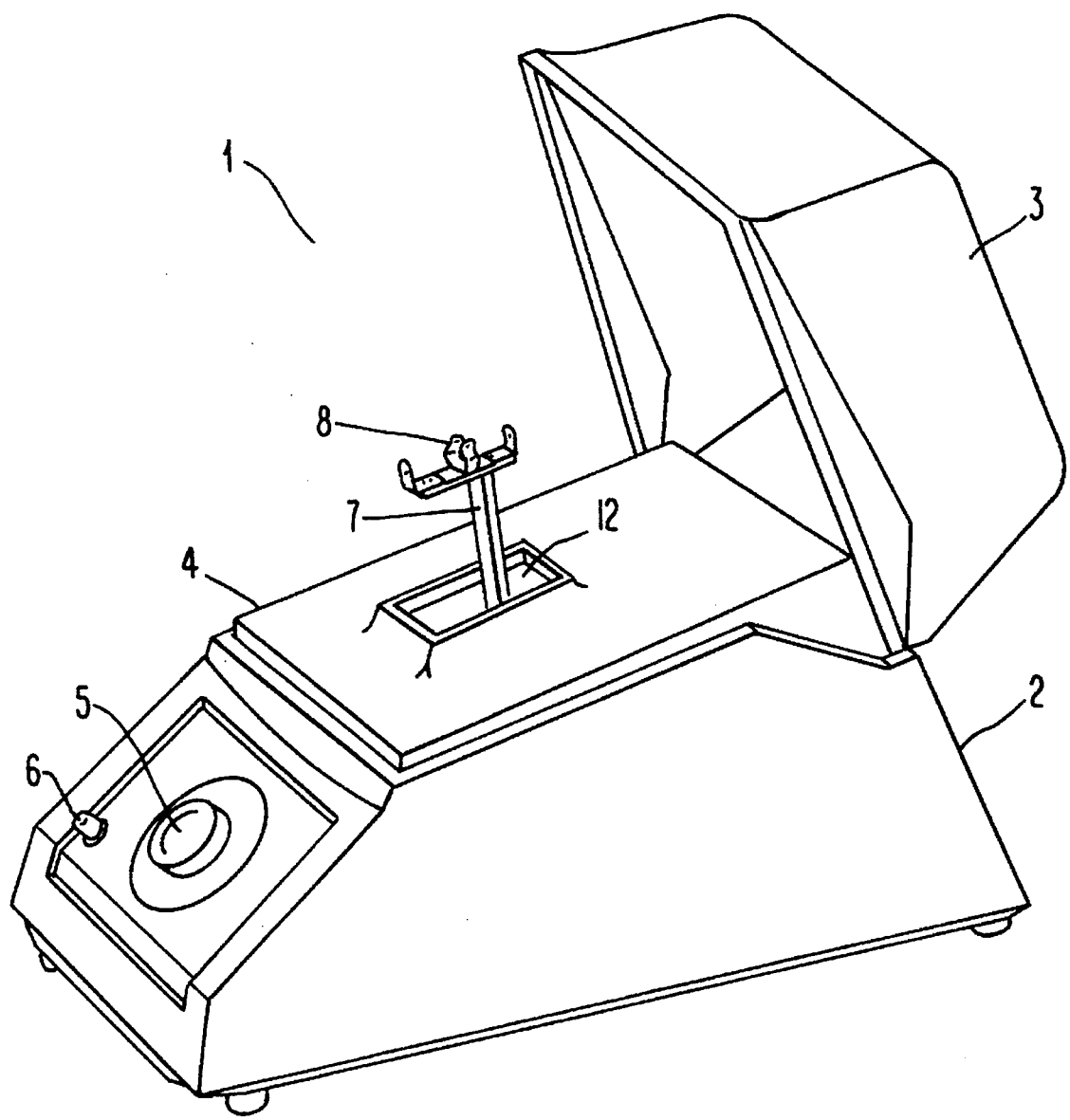
FIG. 2 is an isometric view of the shaking apparatus according to the current invention, without the container.

The preferred shaking device 1 of the current invention is shown in FIGS. 2 and 3. The apparatus is comprised of a base 2 and a hinged safety cover 3. A start-stop button 6 and a speed control dial 5 are mounted on a housing 4 that encloses the base 2. An arm 7 projects upward through an opening 12 in the upper portion of the housing 4. Turning dial 5 clockwise increases the shaking speed while turning the dial counter-clockwise decreases the shaking speed.

According to the current invention, a mounting bracket 8 is attached to the distal end of the arm 7 that allows the container 9, discussed further below, to be secured to the arm. The bracket 8 is fitted with several spring clips 11 and 12 that hold the container 9 securely in place. Alternatively, a thumb screw type bracket could also be used to provide even more secure attachment of the container 9. As shown in FIG. 3, the bracket may be oriented at an angle δ to the horizontal so that, when installed in the device 1, the axis of the container 9 will also be oriented at an angle δ to the horizontal. Preferably, the angle δ is in the range −5° to +5°, and most preferably is about 0°. In use, the container 9 is secured to the bracket 8 and the shaker device 1 is operated to vigorously shake the container along the path of travel shown in FIGS. 4 and 5.

Figure 11:
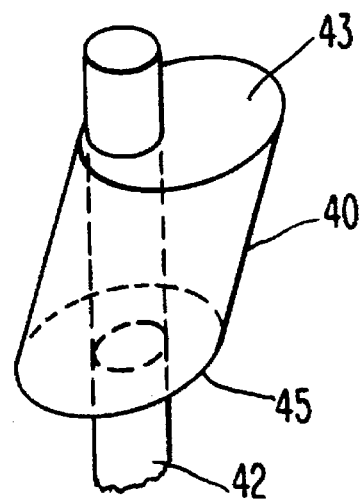
FIG. 11 is an isometric view of the eccentric bushing as mounted on the motor shaft.

FIGS. 6–12 show the major internal components of the shaker device 1 according to the current invention. As can be seen, the shaker arm 7 is rotatably mounted onto the shaft 42 of an electric motor 44. As shown best in FIGS. 6 and 9, a cylindrical sleeve 41 is formed at the proximal end of the shaker arm 7. The sleeve 41 houses a bearing 50 that supports a cylindrical eccentric bushing 40. The bushing 40, shown best in FIG. 11, is fixedly attached to the shaft 42—for example, by being pressed onto or integrally formed with the shaft—and rotates within the bearing 50.

Figure 7:
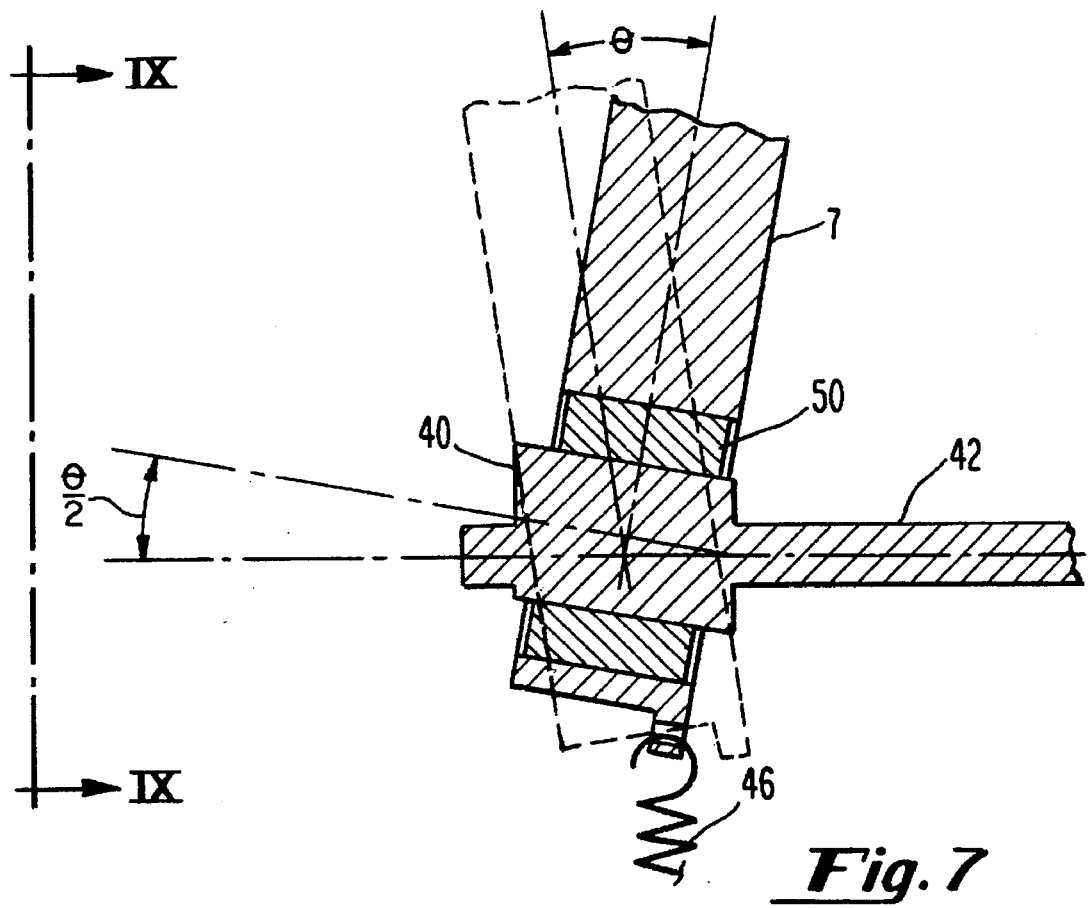
FIGS. 7 and 8 are longitudinal cross-sections through the shaking apparatus shown in FIG. 2 in the vicinity of the region where the shaker arm is mounted onto the motor shaft, with the position of the shaker arm when the eccentric bushing is in the orientation shown in FIG. 8 being shown in phantom in FIG. 7.

As shown best in FIG. 11, one end 43 of the bushing 40 is eccentric with respect to the shaft 42 while the other end 45 of the bushing is concentric with the shaft. Consequently, as shown best in FIG. 7, the center line of the bushing 40 forms an acute angle θ/2 with the center line of shaft 42. The angle θ is referred to as the bearing offset angle. As previously discussed, the bearing offset angle θ is preferably at least about 3°. As shown in FIGS. 7 and 8, as the shaft 42 and bushing 40 rotate 360°, the shaker arm 7 rotates back and forth in the longitudinal plane by an angle that is equal to θ (when the bushing 40 is in the orientation shown in FIG. 8, the position of the shaker arm 7 is as shown in phantom in FIG. 7). Thus, rotary motion of the shaft 42 rotates the sleeve 41 in the longitudinal plane and imparts rectilinear motion along an arcuate path to the distal end of the shaker arm 7 to which the container 9 is secured, as shown in FIG. 4.

Due to the eccentric nature of the bushing 40, rotation of the shaft 42 also tends to rotate the sleeve 41 of the shaker arm 7 through the bearing offset angle θ in the transverse direction as well, as shown in FIG. 10 (the position of the shaker arm when the bushing has been rotated 180° is shown in phantom in FIG. 10). Thus, if the rotation of the shaft 42 were clockwise when viewed from left to right in FIG. 7, then the orientation of the shaker arm 7 when the eccentric bushing 40 is at 0° is shown by the solid lines in FIG. 7, the orientation when the bushing is at 90° is shown in phantom in FIG. 10, the orientation when the bushing is at 180° is shown in FIG. 8, and the orientation when the bushing is at 270° is shown by the solid lines in FIG. 10. Thus, as the eccentric bushing 40 rotates 360° within the bearing 50, the shaker arm 7 imparts a shaking motion to the container 9 in both the longitudinal and transverse directions so as to achieve the figure-8 pattern previously discussed.

Figure 6:
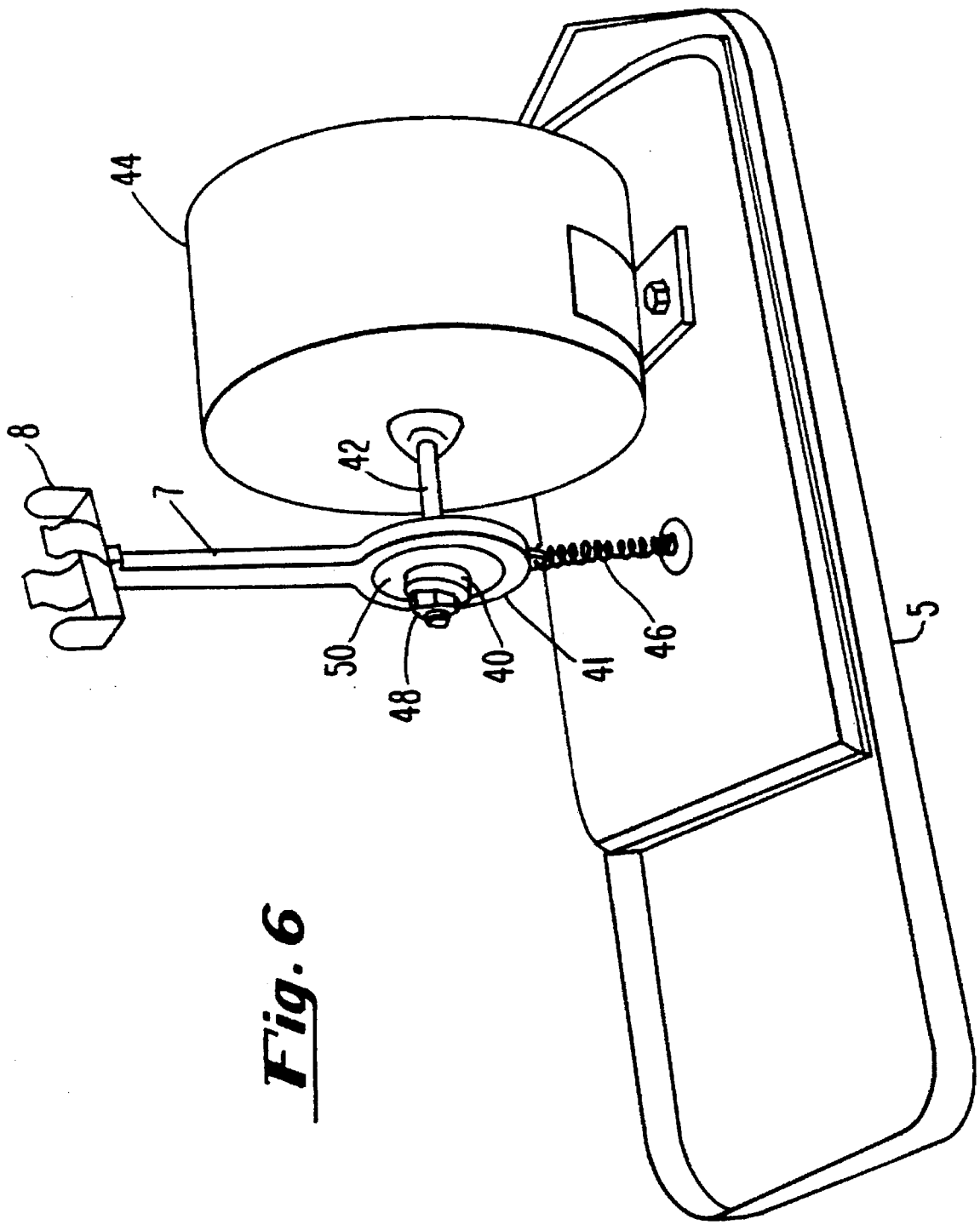
FIG. 6 is an isometric view of the major internal components of the shaking apparatus shown in FIG. 2.

A spring 46 extends from bottom dead center of the sleeve 41 to the base plate 5 of the shaker housing, as shown in FIG. 6. Tension on the spring 46 acts to keep the shaker arm 7 in the upright position as the bushing 40 rotates. Preferably, the spring 46 has sufficient tension so that the shaker arm 7 remains essentially vertically oriented in the transverse plane, as shown in FIGS. 9(a) and (b), although it departs from the vertical by θ/2 in the longitudinal plane, as shown in FIG. 7. Utilizing a spring 46 having a lesser spring constant will allow the shaker arm 7 to rotate in the transverse plane through an angle ω, as shown in FIG. 12. This has the effect of increasing the amplitude in the transverse direction C'.

Preferably, the shaking device 1 is constructed by modifying a commercially available shaking device manufactured by Crescent Dental Manufacturing, Inc., 7750 West 47th Street, Lyons, Ill. 60534 under the name Wig-L-Bug™ 3110B shaker. Such Wig-L-Bug™ devices employ a figure-8 type of shaking pattern and are sold having a shaker arm with a length L of 4 cm, a bearing offset angle and, therefore, a shaker arm angle of rotation in the longitudinal direction θ of 6°, and operate at a fixed speed of 3200 RPM. Further, the shaker arm on the Wig-L-Bug features a pair of spoons to hold the samples.

Thus, the shaking apparatus of the current invention may be created by modifying a Wig-L-Bug™ 3110B shaker to incorporate the container 9, into which the aqueous suspension and gaseous phases have been added, as previously discussed, onto the distal end of the arm 7. Preferably, the Wig-L-Bug™ shaker is also modified so as to incorporate the mounting bracket 8 for securing the container 9 onto the shaker arm 7, as shown in FIGS. 3 and 6. In addition, depending on the composition of the aqueous and gases phases, the size of the container, etc., optimal results may be obtained by further modifying the Wig-L-Bug™ so as to (i) provide shaking at a frequency other than 3200 RPM or to allow operation over a range of shaking frequencies, (ii) employ a shaker arm length other than 4 cm, or (iii) employ a bearing offset angle θ other than 6° by modifying the offset bushing 40.

Other types of reciprocal shaking devices can also be used in the practice of the current invention, most preferably, devices which impart a figure-8 shaking motion. In addition to the Wig-L-Bug™, such devices include (i) the Mixomat, sold by Degussa AG, Frankfurt, Germany, (ii) the Capmix, sold by Espe Fabrik Pharmazeutischer Praeparate GMBH & Co., Seefeld, Oberay Germany, (iii) the Silamat Plus, sold by Vivadent, Lechtenstein, and (iv) the Vibros, sold by Quayle Dental, Sussex, England.

Figure 18A:
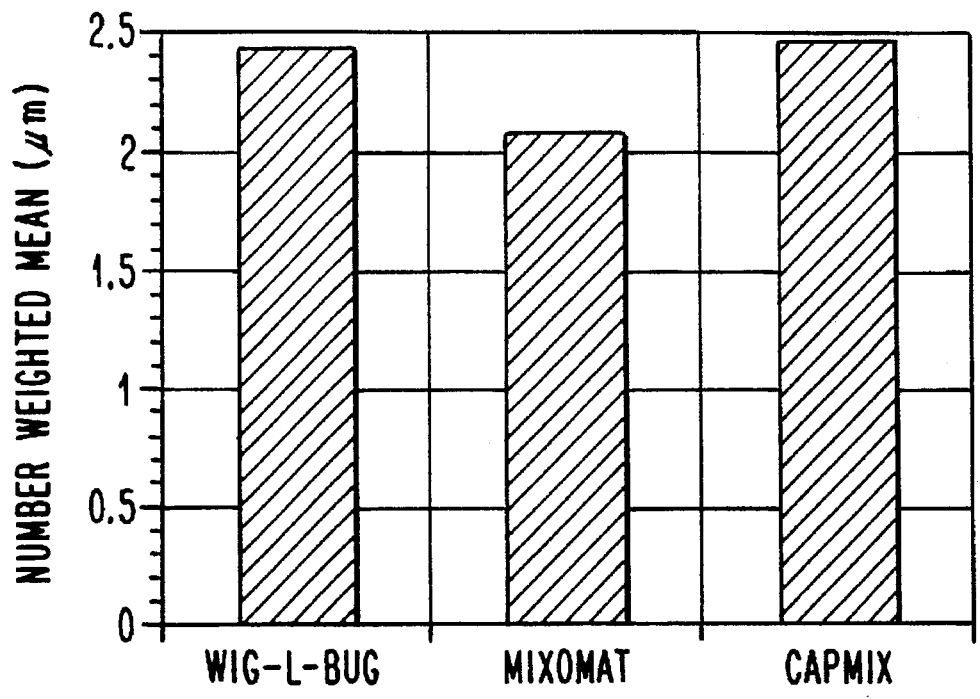
FIGS. 18(a) through 18(c) are charts showing the percentage of the vesicles having a size less than 10 μm, the number weighted mean size, and the particles per mL for three different types of shaking devices.
Figure 18B:
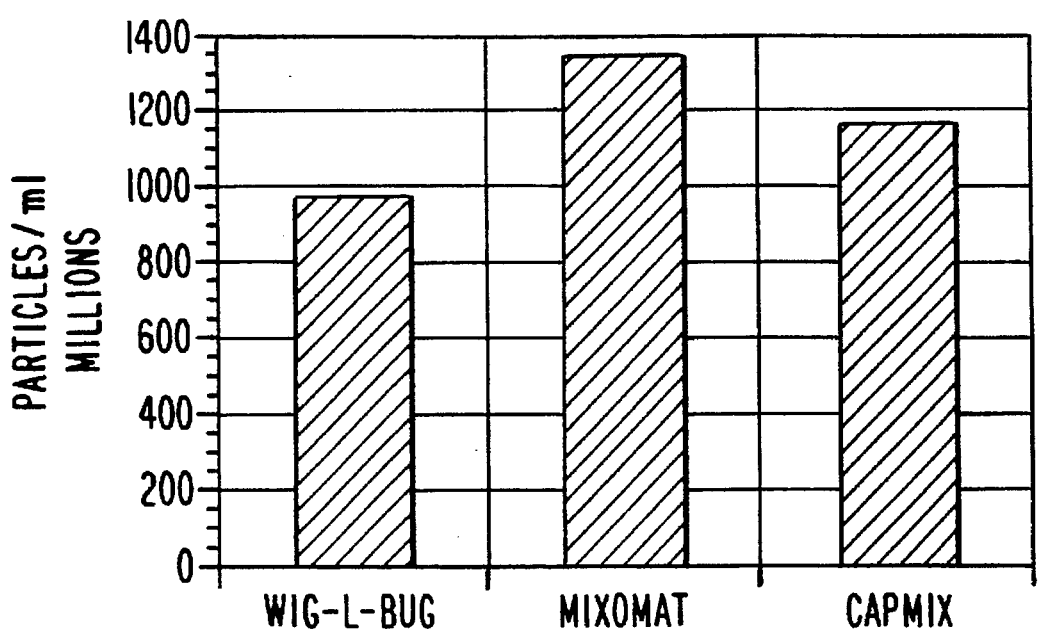
Figure 18C:
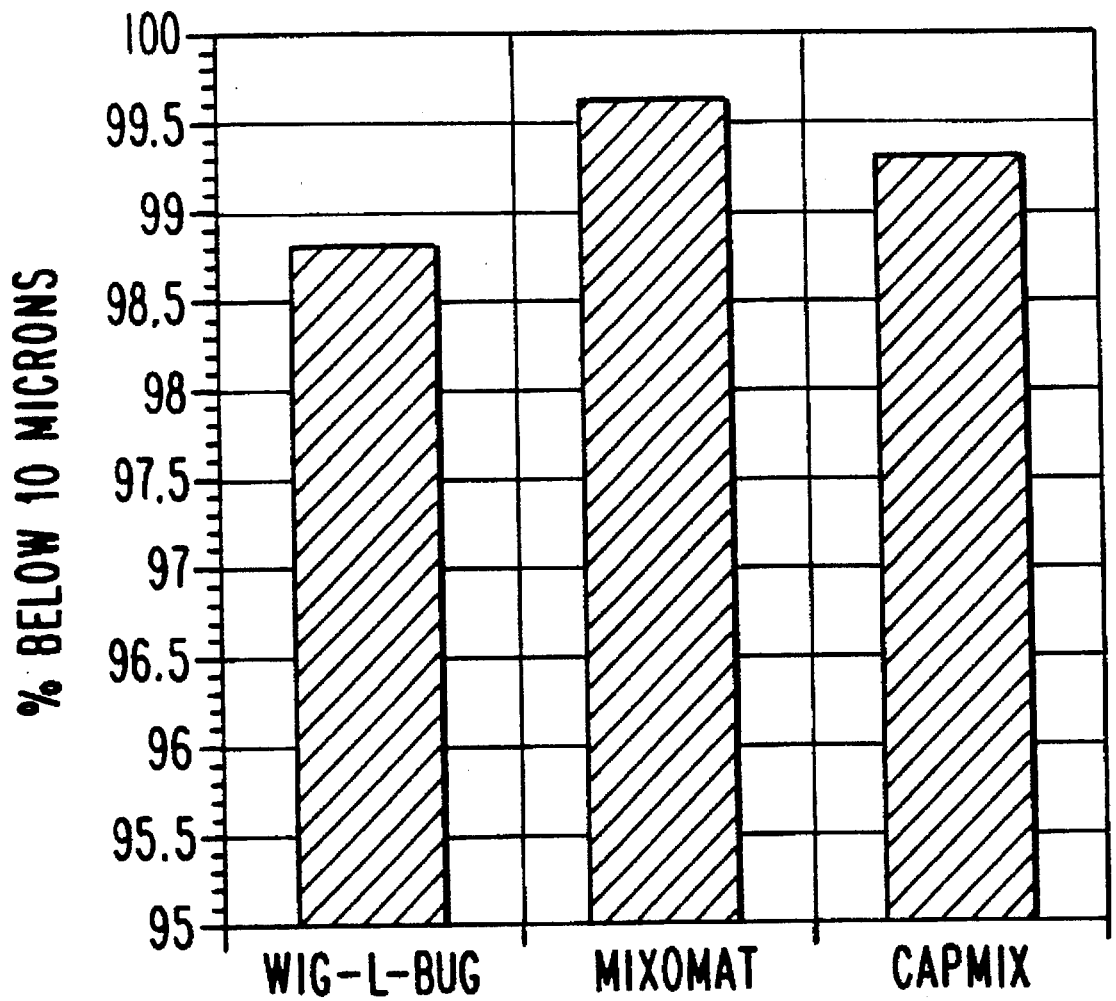

FIGS. 18(a)–(c) show the results of tests on the Mixomat and Capmix compared to test results obtained from a Wig-L-Bug™ 3110B using the same materials and procedures previously discussed with respect to the test results shown in FIGS. 13–17, and a shaking duration of 60 seconds, with the Wig-L-Big™ operating at a frequency of 3200 RPM, the Mixomat operating at a frequency of 4100 RPM, and the Capmix operating at a frequency of 4500 RPM. As can be seen, in each instance, more than 98% of the vesicles were less than 10 μm and more than $800 \times 10^6$ vesicles per mL were produced.

B. THE PREFERRED CONTAINER

According to the current invention, the container that is secured to the shaking device 1 may take a variety of different forms. A preferred container 9 is shown in FIG. 1 and comprises a body 30 and a gas tight cap 10. When filled, the container 9 forms a headspace of gas 32 and an aqueous suspension phase 34 substantially separate from one another. Alternatively, the container may take the form of a pre-filled syringe, which may, if desired, be fitted with one or more filters. Accordingly, the term container, as used herein, includes a syringe. Syringes, filled with an aqueous phase and a headspace of a pre-selected gas, are preferably mounted on the shaking device 1 with their long axes oriented in the transverse direction—that is, perpendicular to the arc length C. After shaking, the gas-filled vesicles are produced in the syringe, ready to use. Regardless of the type of container used, it is preferably sterile, along with its contents.

Although, in general, the invention is practiced with sterile containers wherein the aqueous phase is already present within the container, for selected applications, the stabilizing media may be stored within the container in a dried or lyophilized state. In this case the aqueous solution, e.g. sterile phosphate buffered saline; is added to the sterile container immediately prior to shaking. In so doing, the rehydrated stabilizing media within the aqueous phase will again interact with the gas headspace during shaking so as to produce gas-filled vesicles as above. Rehydration of a dried or lyophilized suspending medium necessarily further complicates the product and is generally undesired but for certain preparations may be useful for further extending the shelf life of the product. For example, certain therapeutic agents such as cyclophosphamide, peptides, and genetic materials (such as DNA), might be hydrolyzed on long term aqueous storage. Rehydration of a previously lyophilized sample to form the aqueous phase and headspace prior to shaking can make it practical to produce gas-filled vesicles containing compounds which otherwise might not have sufficient shelf life.

A variety of different materials may be used to produce the container, such as glass, borosilicate glass, silicate glass, polyethylene, polypropylene, polytetrafluoroethylene, polyacrylates, polystyrene, or other plastics. The preferred containers are either gas impermeable or wrapped within an outer gas impermeable barrier prior to filling with gas. This is, or course, desirable to maintain the integrity of the pre-selected gas within the vessel. Examples of syringe materials having gas-tight capabilities may include but are by no means limited to glass silicates or borosilicates, fitted with silica-fused syringes or luer-lock type syringes, and teflon-tipped or teflon-coated plungers.

The size of the container, more specifically, its weight, will affect the size of the gas-filled vesicles. Shaking devices will generally shake more slowly as the weight of the container increases beyond a certain level—for example, a Wig-L-Bug™ 3110B shakes more quickly with a 2 ml vial (actual volume 3.7 ml) than a 10 ml vial. Therefore, the volume of the container should not exceed a certain amount depending on the particular shaking device utilized.

Tests were performed on a Wig-L-Bug utilizing both a 10 ml clear vial (Wheaton Industries, Millville, N.J.) and a 2 ml (actual volume 3.7 ml) amber vial (Wheaton Industries, Millville, N.J.). Once again, the rate of shaking was measured, using a Code-Palmer Pistol Grip tachometer (Code-Palmer, Nile, Ill.). Table 7 lists the results, which demonstrate that increasing the capacity of the vial will decrease the shaking frequency.

TABLE 7

| Effect of Vial Size on Wig-L-Bug ™ Shaking Frequency | |
|---|---|
| Vial Size | Measured Frequency (RPM) |
| 2 ml vial | 3250 |
| 10 ml vial | 2950 |

As can be seen, a 2 mL nominal provides permits the use of a high shaking frequency on the Wig-L-Bug. With reference to the dimensions shown in FIG. 1, a 2 mL nominal, 3.7 mL actual, container 9 preferably has a diameter D of approximately 0.7 inch, and overall height $H_o$ of approximately 1.4 inch and a body height $H_B$ of approximately 1 inch.

VI. APPLICATIONS OF THE VESICLES PRODUCED ACCORDING TO THE CURRENT INVENTION

The foregoing sets forth various parameters in determining gas-filled vesicle size. Vesicle size is of importance in terms of maximizing product efficacy and minimizing toxicity. Additionally the vesicles should be as flexible as possible both to maximize efficacy and to minimize adverse tissue interactions such as lodging in the lungs. The present invention creates vesicles of the desired size with very thin compliant membranes. Because the vesicle membranes are so thin and compliant, e.g. only 1 mg ml$^{-1}$ of lipid is necessary for stabilizing the membranes, it has been found that gas-filled vesicles of larger diameter may be used without producing pulmonary hypertension. For example, pigs have been administered doses up five time the necessary diagnostic imaging dose without any evidence of pulmonary hypertension. By comparison much lower doses of smaller diameter albumin coated air bubbles in these animals cause severe pulmonary hypertension. Because the vesicles of the present invention are so flexible and deformable, they easily slide through the lung capillaries. Additionally the coating technologies employed with the present lipids polyethyleneglycol bearing lipids) decreases adverse pulmonary interactions while at the same time enhancing the in vitro and in vivo stability and efficacy of the product.

The size of gas-filled vesicles for use as general ultrasound contrast media should be as large as possible (without causing embolic effects) because backscatter or the ultrasound effect is proportional to the radius to the sixth power when frequencies are such that the gas-filled vesicles are in the Rayleigh scattering regime. For MRI, larger vesicles of the invention are also preferred. The ability of the present invention to prepare and employ larger vesicle size with less potential of toxic effects increases its efficacy relative to other products.

An additional parameter influencing ultrasound contrast is the elasticity of the vesicle membrane. The greater the elasticity the greater the contrast effect. Because the present vesicles are coated by ultra-thin membranes of lipid elasticity is quite similar to naked gas and reflectivity and contrast effect are maximized.

The shaking procedure of the present invention readily produces vesicles from an aqueous phase and a headspace of gas within a sterile container. The invention is sufficient for producing vesicles with highly desirable properties for ultrasonic or magnetic resonance imaging applications. For selected applications however, a filter may be employed to produce vesicles with even more homogeneous size distributions and of desired diameters. For example for measuring in vivo pressures on ultrasound using gas-filled vesicle harmonic phenomena, it may be useful to have very tightly defined vesicle diameters within a narrow range of sizes. This is readily accomplished by injecting the vesicles (produced by shaking the container with aqueous phase and headspace of gas) through a filter of defined size. The resulting vesicles will be no larger than a very close approximation of the size of the filter pores in the filter membrane. As noted above, for many ultrasonic or MRI applications, it is desirable to have the gas-filled vesicles be as large as possible. For certain applications however, much smaller gas-filled vesicles may be desirable. In targeting, for example, to tumors or other diseased tissues, it may be necessary for the gas-filled vesicles to leave the vascular space and to enter the tissue interstitium. Much smaller gas-filled vesicles may be useful for these applications. These smaller gas-filled vesicles (e.g., appreciably under a micron in diameter) can to a large extent be produced by modifications in the compounds in the aqueous phase (composition and concentration), as well as the headspace (composition of gas and volume of headspace), but also by injection through a filter. Very small gas-filled vesicles of substantially homogeneous size may be produced by injecting through for example a 0.22 micron filter. The resulting nanometer sized gas-filled vesicles may then have desirable properties for targeting.

The above examples of lipid suspensions may also be sterilized via autoclave without appreciable change in the size of the suspensions. Sterilization of the contrast medium may be accomplished by autoclave and/or sterile filtration performed either before or after the shaking step, or by other means known to those skilled in the art.

After filling the containers with the aqueous phase and the headspace of the pre-selected gas the sealed bottles may be stored indefinitely. There need be no particles to precipitate, gas-filled vesicles to burst or other untoward interactions between gas-filled vesicles, particles, colloids or emulsions. The shelf life of the container filled with the aqueous phase and headspace of gas depends only on the stability of the compounds within the aqueous phase. These properties of long shelf life and sterilizability confer substantial advantages to the present invention over the prior art. The problem of stability, such as with aggregation and precipitation of particles, which was so common in the field of ultrasound contrast media have been addressed herein.

The gas-filled vesicles which are produced by shaking of the multi-phase container of the invention have been found to have excellent utility as contrast agents for diagnostic imaging, such as ultrasound or magnetic resonance imaging. The vesicles are useful in imaging a patient generally, and/or in specifically diagnosing the presence of diseased tissue in a patient. The imaging process may be carried out by administering a gas-filled vesicle of the invention to a patient, and then scanning the patient using ultrasound or magnetic resonance imaging to obtain visible images of an internal region of a patient and/or of any diseased tissue in that region. By region of a patient, it is meant the whole patient, or a particular area or portion of the patient. The liposomal contrast agent may be employed to provide images of the vasculature, heart, liver, and spleen, and in imaging the gastrointestinal region or other body cavities, or in other ways as will be readily apparent to those skilled in the art, such as in tissue characterization, blood pool imaging, etc. Any of the various types of ultrasound or magnetic resonance imaging devices can be employed in the practice of the invention, the particular type or model of the device not being critical to the method of the invention.

The gas-filled vesicles of the invention may also be employed to deliver a wide variety of therapeutics to a patient for the treatment of various diseases, maladies or afflictions, as one skilled in the art will recognize.

Also, magnetically active vesicles may be used for estimating pressure by MRI. The vesicles increase the bulk susceptibility and, accordingly, increase $T_2$ relaxation but even more so for $T_2$* relaxation. Because the effects of static field gradients are mainly compensated in spin echo experiments (by virtue of the 180° radiofrequency refocusing pulse) the effect of the vesicles is less marked On $T_2$ than $T_2$* weighted pulse sequences where static field effects are not compensated. Increasing pressure results in loss of vesicles or vesicle disruption (for more soluble gases) as well as a decrease in vesicle diameter. Accordingly, $1/T_2$ decreases with increasing pressure. After release of pressure some of the remaining vesicles re-expand and $1/T_2$ increases again slightly. Vesicles composed of about 80% PFP with 20% air show enhanced stability and a slight fall in $1/T_2$ with pressure which returns to baseline after release of pressure (i.e., the vesicles are stable but show a slight $1/T_2$ pressure effect). When gradient echo images are obtained and signal intensity measured these effects are much more marked. Signal intensity increases with increasing pressure ($1/T_2$, decreases with increased pressure). Because the experiment is performed relatively quickly (it takes less than a tenth the time to perform the gradient echo images than to measure $T_2$). The duration of exposure to pressure is much less and the nitrogen filled vesicles return nearly to baseline after pressure release (i.e. there is very little loss of vesicles). Accordingly, the signal intensity on gradient echo falls back nearly to baseline at return to ambient pressure. For measurement of pressure by MRI, the vesicles may be designed either to fall apart with increasing pressure or to be stable but decrease vesicle diameter with increasing pressure. Because on MRI vesicle radius affects $1/T_2^*$, this relationship can be used to estimate pressure by MRI.

As one skilled in the art would recognize, administration of the gas-filled vesicles to the patient may be carried out in various fashions, such as intravenously or intraarterially by injection, orally, or rectally. The useful dosage to be administered and the particular mode of administration will vary depending upon the age, weight and the particular mammal and region thereof to be scanned or treated, and the particular contrast medium or therapeutic to be employed. Typically, dosage is initiated at lower levels and increased until the desired contrast enhancement or therapeutic effect is achieved. The patient can be any type of mammal, but most preferably is a human.

The disclosures of each of the patents and publications cited or referred to herein are hereby incorporated herein by reference in their entirety.

Various modifications of the invention in addition to those shown and described herein will be apparent to those skilled in the art from the foregoing description. Such modifications are also intended to fall within the scope of the appended claims.

What is claimed:

1. A method of making vesicles, comprising the steps of:
   a) placing an aqueous suspension phase and a gaseous phase substantially separate from said aqueous suspension phase in a container; and
   b) shaking said container by imparting a reciprocating motion thereto until vesicles are formed.

2. The method according to claim 1, wherein the amplitude of said reciprocating motion is at least approximately 0.3 cm.

3. The method according to claim 2, wherein the amplitude of said reciprocating motion is no greater than approximately 2.5 cm.

4. The method according to claim 1, wherein the total length of travel of said container during said reciprocating motion is at least approximately 0.7 cm.

5. The method according to claim 1, wherein the frequency of said reciprocating motion is at least approximately 2800 RPM.

6. The method according to claim 2, wherein the frequency of said reciprocating motion is no greater than approximately 4500 RPM.

7. The method according to claim 1, wherein said reciprocating motion occurs in at least a first direction, said motion in said first direction occurring along an arcuate path.

8. The method according to claim 7, wherein the angle of rotation encompassed by said arcuate path is at least approximately 3°.

9. The method according to claim 8, wherein the angle encompassed by said arcuate path is no greater than approximately 9°.

10. The method according to claim 7, wherein the radius of curvature of said arcuate path is at least approximately 6 cm.

11. The method according to claim 10, wherein the radius of curvature of said arcuate path is no greater than approximately 15 cm.

12. The method according to claim 1, wherein said reciprocating motion comprises motion in first and second substantially perpendicular directions.

13. The method according to claim 12, wherein said reciprocating motion occurs along a path having approximately a figure-8 pattern.

14. The method according to claim 13, wherein the total length of travel of said container around said figure-8 pattern is at least approximately 0.7 cm.

15. The method according to claim 1, wherein said aqueous suspension phase comprises lipids.

16. The method according to claim 15, wherein said aqueous suspension phase comprises
dipalmitoylphosphatidylcholine, dipalmitoylphosphatidic acid, and dipalmitoylphosphatidylethanolamine.

17. The method according to claim 16, wherein said gaseous phase comprises a perfluorocarbon gas.

18. The method according to claim 1, wherein said gas phase initially occupies at least 10% of the volume of said container.

19. The method according to claim 1, wherein said shaking produces vesicles of which 95% are smaller than 10 µm.

20. The method according to claim 19, wherein the duration of said shaking is no greater than approximately 2 minutes.

21. The method according to claim 1, wherein said shaking produces vesicles having a mean size of less than 2.5 µm.

22. The method according to claim 1, wherein said container is a syringe.

23. The method according to claim 1 wherein said vesicles comprise a monolayer.

24. The method according to claim 23 wherein said monolayer comprises a phospholipid.

25. The method according to claim 24 wherein said gaseous phase is selected from the group consisting of perfluoropropane, perfluorobutane, perfluoropentane, perfluorohexane, and sulfur hexafluoride.

26. The method according to claim 24 wherein said monolayer comprises a phospholipid and said gaseous phase is perfluoropentane.

27. The method according to claim 24 wherein said monolayer comprises a phospholipid and said gaseous phase is sulfur hexafluoride.

28. The method according to claim 24 wherein said monolayer comprises a phospholipid and said gaseous phase is perfluoropropane.

29. The method according to claim 1 wherein said vesicles comprise a polymer.

30. The method according to claim 29 wherein said polymer comprises an acrylate.

31. The method according to claim 30 wherein said gas is air.

32. The method according to claim 29 wherein said polymer comprises a methacrylate.

33. The method according to claim 32 wherein said gas is air.

34. The method according to claim 1 wherein said vesicles comprise a polysaccharide.

35. The method according to claim 34 wherein said polysaccharide comprises galactose.

36. The method according to claim 35 wherein said gaseous phase is nitrogen.

37. The method according to claim 15 wherein said aqueous suspension phase comprises liposomes.

38. The method according to claim 37 wherein said liposomes comprise cross-linked liposomes or polymerized liposomes.

39. The method according to claim 15 wherein said aqueous suspension phase further comprises polyethylene glycol.

* * * * *

UNITED STATES PATENT AND TRADEMARK OFFICE
CERTIFICATE OF CORRECTION

PATENT NO. : 5,656,211            Page 1 of 4

DATED : Aug. 12, 1997

INVENTOR(S) : Unger et al.

It is certified that error appears in the above-identified patent and that said Letters Patent is hereby corrected as shown below:

On the title page, at [63], in the "Related U.S. Application Data" section, first line thereof, please delete "Sep. 19, 1994" and insert --Sep. 16, 1994-- therefor.

On the title page, at [63], in the "Related U.S. Application Data" section, second line thereof, please delete "Pat No. 5,542,938" and insert --Pat No. 5,542,935-- therefor.

On the title page, at [63], in the "Related U.S. Application Data" section, third line thereof, please insert --Pat No. 5,580,575-- at the end of the line, after "Jun. 11, 1993.".

On the title page, at [63], in the "Related U.S. Application Data" section, seventh line thereof, please insert --Pat. No. 5,585,112-- after "Nov. 30, 1993,".

On the title page, at [63], in the "Related U.S. Application Data" section, ninth line thereof, please delete "abandoned," and insert --Pat No. 5,469,854,-- therefor.

On the title page, at [63], in the "Related U.S. Application Data" section, tenth line thereof, please insert --Jun. 18, 1991, Pat No. 5,228,446,-- after "717,084,".

On the title page, at [63], in the "Related U.S. Application Data" section, line tenth line thereof, please insert --Jun. 18, 1991, abandoned,-- after "716,899,".

UNITED STATES PATENT AND TRADEMARK OFFICE
CERTIFICATE OF CORRECTION

PATENT NO. : 5,656,211
DATED : Aug. 12, 1997
INVENTOR(S) : Unger et al.

It is certified that error appears in the above-indentified patent and that said Letters Patent is hereby corrected as shown below:

On page 2, column 1, in the "U.S. PATENT DOCUMENTS" section, at "4,569,836", please insert --424/1.1-- at the end of the line.

On page 3, column 1, in the "OTHER PUBLICATIONS" section, first line thereof at Thanassi, please delete "Thanassi,37 Aminomalonic" and insert --Thanassi, "Aminomalonic-- therefor.

On page 4, column 1, in the "OTHER PUBLICATIONS" section, at Poznansky, please delete " "Biologica " and insert --"Biological-- therefor.

In column 1, line 7, please delete "Sep. 19, 1994," and insert --Sep. 16, 1994,-- therefor.

In column 2, line 28, please delete "imagining." and insert --imaging.-- therefor.

In column 8, line 15, please delete "carboxmthylcel-" and insert -- carboxymethylcel- -- therefor.

In column 9, line 33, please delete the second occurrence of "such as".

In column 13, line 64, please delete "decafluorousobutane" and insert --decafluoroisobutane-- therefor.

UNITED STATES PATENT AND TRADEMARK OFFICE
CERTIFICATE OF CORRECTION

PATENT NO. : 5,656,211
DATED : Aug. 12, 1997
INVENTOR(S) : Unger et al.

It is certified that error appears in the above-indentified patent and that said Letters Patent is hereby corrected as shown below:

In column 15, line 30, lease delete "of a gas-filled" and insert --of gas-filled-- therefor.

In column 17, line 14, please delete "softward." and insert --software.-- therefor.

In column 17, line 22, please delete "above" and insert --below-- therefor.

In column 18, line 13, please delete "gas in added." and insert --gas is added.-- therefor.

In column 22, line 8, please delete "move" and insert --moves-- therefor.

In column 22, line 44, please delete "L ms" and insert --L is-- therefor.

In column 28, line 21, please delete "or course," and insert --of course,-- therefor.

In column 28, line 52, please delete "provides".

In column 29, line 6, please delete "up five time" and insert --up to five times-- therefor.

UNITED STATES PATENT AND TRADEMARK OFFICE
CERTIFICATE OF CORRECTION

PATENT NO. : 5,656,211
DATED : Aug. 12, 1997
INVENTOR(S) : Unger et al.

It is certified that error appears in the above-indentified patent and that said Letters Patent is hereby corrected as shown below:

In column 29, line 13, please insert --(e.g.-- after "lipids" and before "polyethyleneglycol".

In column 30, line 46, please delete "marked On" and insert --marked on-- therefor.

In column 30, line 58, please delete "(1/$T_2$," and insert --(1/$T_2$*-- therefor.

Signed and Sealed this

Third Day of March, 1998

Attest:

BRUCE LEHMAN

Attesting Officer

Commissioner of Patents and Trademarks